United States Patent
Fang et al.

(10) Patent No.: US 7,662,623 B2
(45) Date of Patent: *Feb. 16, 2010

(54) COMPOSITIONS AND METHODS FOR ENHANCED EXPRESSION OF RECOMBINANT POLYPEPTIDES FROM A SINGLE VECTOR USING A PEPTIDE CLEAVAGE SITE

(75) Inventors: Jianmin Fang, Foster City, CA (US); Karin Jooss, Bellevue, WA (US); Andrew Simmons, San Mateo, CA (US); Jing-Jing Qian, Foster City, CA (US)

(73) Assignee: BioSante Pharmaceuticals, Inc., Lincolnshire, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/977,787

(22) Filed: Oct. 26, 2007

(65) Prior Publication Data
US 2008/0280356 A1  Nov. 13, 2008

Related U.S. Application Data

(63) Continuation of application No. 10/831,304, filed on Apr. 26, 2004.

(60) Provisional application No. 60/540,553, filed on Feb. 2, 2004.

(51) Int. Cl.
*C12N 15/00* (2006.01)
*C12N 15/11* (2006.01)
*C12N 15/13* (2006.01)
*C12P 21/08* (2006.01)

(52) U.S. Cl. .................. 435/320.1; 435/69.1; 536/23.1; 536/23.53; 536/24.1; 536/24.2

(58) Field of Classification Search ........................ None
See application file for complete search history.

(56) References Cited

U.S. PATENT DOCUMENTS

| | | | |
|---|---|---|---|
| 5,310,903 A | 5/1994 | Goulet et al. |
| 5,362,718 A | 11/1994 | Skotnicki et al. |
| 5,436,146 A | 7/1995 | Shenk et al. |
| 5,525,610 A | 6/1996 | Caufield et al. |
| 5,573,500 A | 11/1996 | Katsunuma |
| 5,643,745 A | 7/1997 | Stuart |
| 5,686,279 A | 11/1997 | Finer et al. |
| 5,753,500 A | 5/1998 | Shenk et al. |
| 5,846,767 A | 12/1998 | Halpin et al. |
| 5,863,765 A | 1/1999 | Berry et al. |
| 5,872,005 A | 2/1999 | Wang et al. |
| 5,994,106 A | 11/1999 | Kovesdi et al. |
| 6,015,709 A | 1/2000 | Natesan |
| 6,040,183 A | 3/2000 | Ferrari et al. |
| 6,093,570 A | 7/2000 | Ferrari et al. |
| 6,117,680 A | 9/2000 | Natesan et al. |
| 6,127,175 A | 10/2000 | Vigne et al. |
| 6,133,028 A | 10/2000 | Imler et al. |
| 6,133,456 A | 10/2000 | Holt et al. |
| 6,150,527 A | 11/2000 | Holt et al. |
| 6,171,586 B1 | 1/2001 | Lam et al. |
| 6,180,371 B1 | 1/2001 | Lollar |
| 6,187,757 B1 | 2/2001 | Clackson et al. |
| 6,200,560 B1 | 3/2001 | Couto et al. |
| 6,221,349 B1 | 4/2001 | Couto et al. |
| 6,251,632 B1 | 6/2001 | Lillicrap et al. |
| 6,261,567 B1 | 7/2001 | Hart et al. |
| 6,271,025 B1 | 8/2001 | Negrier et al. |
| 6,306,649 B1 | 10/2001 | Gilman et al. |
| 6,320,029 B1 | 11/2001 | Miekka et al. |
| 6,331,415 B1 | 12/2001 | Cabilly et al. |
| 6,358,703 B1 | 3/2002 | Cho et al. |
| 6,376,463 B1 | 4/2002 | Lollar |
| 6,458,563 B1 | 10/2002 | Lollar |
| 6,479,653 B1 | 11/2002 | Natesan et al. |
| 6,506,379 B1 | 1/2003 | Clackson et al. |
| 6,517,830 B1 | 2/2003 | Lollar et al. |

(Continued)

FOREIGN PATENT DOCUMENTS

| | | |
|---|---|---|
| EP | 0623679 | 11/1994 |
| ES | 2172383 | 9/2002 |
| WO | WO 92/08793 | 5/1992 |
| WO | WO95/21249 | 8/1995 |
| WO | WO 97/28272 | 8/1997 |
| WO | WO97/49725 | 12/1997 |
| WO | WO99/46274 | 9/1999 |
| WO | WO99/46299 | 9/1999 |
| WO | WO99/61595 | 12/1999 |
| WO | WO99/61642 | 12/1999 |

(Continued)

OTHER PUBLICATIONS

Altschul, 1997, Gapped BLAST and PSI-BLAST: a new generation of protein database search programs, Nucl Acid Res. 25(17):3389-3402.

(Continued)

*Primary Examiner*—Maria B Marvich
(74) *Attorney, Agent, or Firm*—Ropes & Gray LLP; James F. Haley, Jr.; Teresa A. Chen

(57) ABSTRACT

Vector constructs for expression of two or more functional proteins or polypeptides under operative control of a single promoter and methods of making and using the same are described. The vectors comprise a self-processing cleavage site between each respective protein or polypeptide coding sequence. The vector constructs include the coding sequence for a self-processing cleavage site and may further include an additional proteolytic cleavage sequence which provides a means to remove the self processing peptide sequence from expressed protein(s) or polypeptide(s). The vector constructs find utility in methods for enhanced production of biologically active proteins and polypeptides in vitro and in vivo.

6 Claims, 14 Drawing Sheets

U.S. PATENT DOCUMENTS

| | | | |
|---|---|---|---|
| 6,518,482 | B2 | 2/2003 | Lubon et al. |
| 6,548,286 | B1 | 4/2003 | Samulski et al. |
| 6,599,724 | B1 | 7/2003 | Mikaelsson et al. |
| 6,602,503 | B1 | 8/2003 | Lobb et al. |
| 6,623,940 | B1 | 9/2003 | Ledbetter et al. |
| 6,632,800 | B1 | 10/2003 | Russell et al. |
| 6,642,028 | B1 | 11/2003 | Ill et al. |
| 6,649,375 | B2 | 11/2003 | Connelly et al. |
| 6,649,595 | B2 | 11/2003 | Clackson et al. |
| 6,692,736 | B2 | 2/2004 | Yu et al. |
| 6,852,510 | B2 | 2/2005 | Bremel et al. |
| 6,911,200 | B2 | 6/2005 | Yu et al. |
| 6,933,362 | B1 | 8/2005 | Belfort et al. |
| 7,001,596 | B1 | 2/2006 | Johnson et al. |
| 7,485,291 | B2 | 2/2009 | Fang et al. |
| 7,498,024 | B2 | 3/2009 | Fang et al. |
| 2002/0168339 | A1 | 11/2002 | Piechacyk et al. |
| 2002/0168342 | A1 | 11/2002 | Wang et al. |
| 2003/0068307 | A1 | 4/2003 | Yu et al. |
| 2003/0083290 | A1 | 5/2003 | Kingsman et al. |
| 2003/0099616 | A1 | 5/2003 | Irving et al. |
| 2003/0099932 | A1 | 5/2003 | Lorens et al. |
| 2004/0086485 | A1 | 5/2004 | Aguilar-Cordova |
| 2004/0131591 | A1 | 7/2004 | Kingsman et al. |
| 2004/0209830 | A1 | 10/2004 | Russell et al. |
| 2004/0235011 | A1 | 11/2004 | Cooper et al. |
| 2004/0235173 | A1 | 11/2004 | Bleck et al. |
| 2004/0265955 | A1 | 12/2004 | Fang et al. |
| 2005/0003482 | A1 | 1/2005 | Fang et al. |
| 2005/0042721 | A1 | 2/2005 | Fang et al. |
| 2005/0095705 | A1 | 5/2005 | Kadan et al. |
| 2005/0136035 | A1 | 6/2005 | Fang et al. |
| 2006/0034805 | A1 | 2/2006 | Fang et al. |
| 2006/0228336 | A1 | 10/2006 | Ko |
| 2006/0292682 | A1 | 12/2006 | Hawkins et al. |
| 2007/0059820 | A1 | 3/2007 | Fang et al. |
| 2007/0065912 | A1 | 3/2007 | Carson et al. |
| 2007/0275915 | A1 | 11/2007 | Hallenbeck et al. |
| 2007/0292922 | A1 | 12/2007 | Fang et al. |
| 2008/0280356 | A1 | 11/2008 | Fang et al. |

FOREIGN PATENT DOCUMENTS

| | | |
|---|---|---|
| WO | WO00/23116 | 4/2000 |
| WO | WO00/71141 | 11/2000 |
| WO | WO01/03726 | 1/2001 |
| WO | WO01/27303 | 4/2001 |
| WO | WO01/45510 | 6/2001 |
| WO | WO01/68109 | 9/2001 |
| WO | WO01/70763 | 9/2001 |
| WO | WO02/24723 | 3/2002 |
| WO | WO02/072023 | 9/2002 |
| WO | WO03/031598 | 4/2003 |
| WO | WO03/047507 | 6/2003 |
| WO | WO03/080108 | 10/2003 |
| WO | WO03/087161 | 10/2003 |
| WO | WO03/100053 | 12/2003 |
| WO | WO2004/092348 | 10/2004 |
| WO | WO 2004/113493 | 12/2004 |
| WO | WO 2007/126805 | 11/2007 |

OTHER PUBLICATIONS

Altshul et al., 1990, Basic local alignment search tool, J. Mol. Biol. 215:403-410.

Bernstein et al., 1997, PDGF2/c-sis mRNA leader contains a differentiation-linked internal ribosomal entry site (D-IRES, J. Biol. Chem. 272(14):9356-9362.

Borman et al., 1994, Sequences within the poliovirus internal ribosome entry segment control viral RNA synthesis, EMBO J. 13(13):3149-3157.

Brinkhous et al., 2002, Preclinical pharmacology of albumin-free B-domain deleted recombinant factor VIII, Semin Thromb Hemos 28(3):269-72 (Abstract Only).

Burton et al., 1999, Coexpression of factor VIII heavy and light chain adeno-associated viral vectors produces biologically active protein, Proc. Natl. Acad. Sci. USA, 96(22):12725-12730.

Capecchi,1980, High efficiency transformation by direct microinjection of DNA into cultured mammalian cells, Cell 22:479-488.

Chaplin et al., 1999, Production of interleukin-12 as a self-processing 2A polypeptide, J. Interferon and Cytokine Res. 19:235-241.

Chazenbalk et al., 1996, Evidence for negative cooperativity among human thyrotropin receptors overexpressed in mammalian cells, Endocrinology 137:4586-4591.

De Felipe et al., 1999, Use of the 2A sequence from foot-and-mouth disease virus in the generation of retroviral vectors for gene therapy, Gene Therapy 6:198-208.

De Felipe et al., 2003, Co-translational, intraribosomal cleavage of polypeptides by the foot-and-mouth disease virus 2A peptide, J. Biol. Chem 78(13):11441-11448.

De Felipe et al., 2004, Targeting of proteins derived from self-processing polyproteins containing multiple signal sequences, Traffic 5:616-26.

De Felipe, 2000, Tricistronic and tetracistronic retroviral vectors for gene transfer, Human Gene Therapy 11:1921-1931.

Donnelly et al., 2001, The 'cleavage' activities of foot-and-mouth disease virus 2A site-directed mutants and naturally occurring '2A-like' sequences, J. Gen. Virol. 82:1027-1041.

Donnelly et al., 2001, Analysis of the aphthovirus 2A/2B polyprotein 'cleavage' mechanism indicates not a proteolytic reaction, but a novel translational effect: a putative ribosomal 'skip', J.Gen. Virol. 82:1013-1025.

Donnolly et al., 1997, The cleavage activities of aphthovirus and cardiovirus 2A proteins, J. Gen Virol 78:13-21.

Duke et al., 1992, Sequence and structural elements that contribute to efficient encephalomyocarditis virus RNA translation, J. Virol. 66(3):1602-1609.

Dull et al., 1998, A third-generation lentivirus vector with a conditional packaging system, J. Virol. 72(11):8463-8471.

Eriksson et al., 2001, The manufacturing process for B-domain deleted recombinant factor VIII, Semin. Hematol. 38:24-31 (Abstract).

Fang, et al., 2005, Stable antibody expression at therapeutic levels using the 2A peptide, Nature Biotechnology, 23(5): 584-590.

Felgner et al., 1987, Lipofection: a highly efficient, lipid-mediated DNA-transfection procedure, Proc. Natl. Acad. Sci. USA 84:7413-7417.

Frolov et al., 1998, cis-acting RNA elements required for replication of bovine viral diarrhea virus-hepatitis C virus 5' nontranslated region chimeras, RNA 4:1418-1435.

Furler et al., 2001, Recombinant AAV vectors containing the foot and mouth disease virus 2A sequence confer efficient bicistronic gene expression in cultured cells and rat substantia nigra neurons, Gene Therapy 8:864-873.

Gaken et al., 2000, Fusagene vectors: a novel strategy for the expression of multiple genes from a single cistron, Gene Therapy 7:1979-1985.

Gan et al., 1996, Internal initiation of translation directed by the 5'-untranslated region of the mRNA for eIF4G, a factor involved in the picornavirus-induced switch from cap-dependent to internal initiation, J. Biol. Chem. 271(2):623-626.

Gengrinovitch et al., 1995, Platelet factor-4 inhibits the mitogenic activity of VEGF121 and VEGF165 using several concurrent mechanisms, J. Biol. Chem. 270:15059-15065.

Ghosh et al., 2002, Baculovirus as mammalian cell expression vector for gene therapy: an emerging strategy, Mol. Ther. 6(1):5-11.

Glass et al., 1993, Identification of the hepatitis A virus internal ribosome entry site: in vivo and in vitro analysis of bicistronic RNAs containing the HAV 5' noncoding region, Virology 193:842-852.

Green et al., 1994, Antigen-specific human monoclonal antibodies from mice engineered with human Ig heavy and light chain YACs, Nat. Genetics 7(1):13-21.

Green, 1999, Antibody engineering via genetic engineering of the mouse: XenoMouse strains are a vehicle for the facile generation of therapeutic human monoclonal antibodies, J. Immunol. Meth. 231:11-23.

Guo et al., 1996, Evaluation of promoter strength for hepatic gene expression in vivo following adenovirus-mediated gene transfer, Gene Ther. 3:802-810.

Gura, 2002, Therapeutic antibodies: magic bullets hit the target, Nature 417:584-586.

Hagedom, 2002, Domain swapping in a COOH-terminal fragment of platelet factor 4 generates potent angiogenesis inhibitors, Cancer Res. 62:6884-6890.

Halpin et al., 1999, Self-processing 2A-polyproteins—a system for co-ordinate expression of multiple proteins in transgenic plants, The Plant Journal 17(4):453-459.

Hamstra and Rehemtulla, 1999, Toward an enzyme/prodrug strategy for cancer gene therapy: endogenous activation of carboxypeptidase A mutants by the PACE/Furin family of propeptidases, Hum. Gene Ther. 10:235-248.

Hartley et al., 1976, Naturally occurring murine leukemia viruses in wild mice: characterization of a new "amphotropic" class, J. Virol. 19(1):19-25.

High, 2003, Gene transfer as an approach to treating hemophilia, Semin. Thromb. Hemost. 29(1):107-20.

Hitt et al., 2000, Adenovirus vectors for human gene therapy, Adv. Virus Res. 55:479-505.

Holash et al., 2002, VEGF-Trap: a VEGF blocker with potent antitumor effects, Proc. Natl. Acad. Sci. USA 99(17):11393-98.

Hosaka et al., 1991, Arg-X-Lys/Arg-Arg motif as a signal for precursor cleavage catalyzed by furin within the constitutive secretory pathway, J. Biol. Chem. 266 19 :12127-12130.

Houdebine, 2002, Antibody manufacture in transgenic animals and comparisons with other systems, Opin. Biotech. 13:625-629.

Huez et al., 1998, Two independent internal ribosome entry sites are involved in translation initiation of vascular endothelial growth factor mRNA, Mol. Cell Biol. 18(11):6178-6190.

Ikonomou et al., 2003, Insect cell culture for industrial production of recombinant proteins, Appl. Microbiol. Biotech. 62(1):1-20.

III et al., 1997, Optimization of the human factor VII complementary DNA expression plasmid for gene therapy of hemophilia A, Blood Coag. Fib. 8(2):S23-S30.

Jackson et al., 1990, The novel mechanism of initiation of picornavirus RNA translation, Trends Biochem. Sci. 15(12):477-83.

Jackson et al., 1995, Internal initiation of translation in eukaryotes: the picornavirus paradigm and beyond, RNA 1(10):985-1000.

Jakobovits et al., 1995, Production of fully human antibodies by transgenic mice, Curr. Opin. in Bio. 6(5):561-566.

Jakobovits et al., 1998, Production and selection of antigen-specific fully human monoclonal antibodies from mice engineered with human Ig loci, Adv. Drug Deliv. Rev. 31:33-42.

Jang et al.,1990, Cap-independent translation of encephalomyocarditis virus RNA: structural elements of the internal ribosomal entry site and involvement of a cellular 57-kD RNA-binding protein, Genes & Dev. 4:1560-1572.

Kim et al., 1990, Use of the human elongation factor 1 alpha promoter as a versatile and efficient expression system, Gene 91:217-23.

Kjalke et al., 1995, Amino acid residues 721-729 are required for full factor VIII activity, Eur. J. Biochem. 234(3):773-779.

Klein et al., 1987, High-velocity microprojectiles for delivering nucleic acids into living cells, Nature 327:70-73.

Knott et al., 2002, Tetracycline-dependent gene regulation: combinations of transregulators yield a variety of expression windows, Biotechniques 32(4):796-800.

Kohler et al., 1976, Derivation of specific antibody-producing tissue culture and tumor lines by cell fusion, Eur. J. Immunol. 6:511-519.

Kolber et al., 1995, Inhibition of development of murine melanoma lung metastases by systemic administration of recombinant platelet factor 4, J. Natl. Cancer Instit.87:304-309.

Kotin, 1994, Prospects for the use of adeno-associated virus as a vector for human gene therapy, Hum. Gene Ther. 5:793-801.

Lamikama et al., 2005, In vivo evaluation of an EIAV vector for the systemic genetic delivery of therapeutic antibodies, Gene Therapy 12:988-998.

Lenting et al., 1998, The life cycle of coagulation factor VIII in view of its structure and function, Blood 92(11):3983-3996.

Lind et al., 1995, Novel forms of B-domain-deleted recombinant factor VIII molecules. Construction and biochemical characterization, Eur. J. Biochem. 232:19-27.

Little et al., 2000, Of mice and men: hybridoma and recombinant antibodies, Immunol. Today 21(8):364-70.

Liu et al., 1999, Hydrodynamics-based transfection in animals by systemic administration of plasmid DNA, Gene Ther. 6:1258-1266.

Lopez-Lastra et al., 1997, Characterization of an internal ribosomal entry segment within the 5' leader of avian reticuloendotheliosis virus type A RNA and development of novel MLV-REV-based retroviral vectors, Hum. Gene Ther. 8:1855-1865.

Macejak et al., 1991, Internal initiation of translation mediated by the 5' leader of a cellular mRNA, *Leishmania* RNA virus 1-mediated cap-independent translation, Nature 353:90-94.

Maga et al., 1995, *Leishmania* RNA virus 1-mediated cap-independent translation, Mol. Cell. Biol. 15(9):4884-4889.

Mah, et al., 2003, Dual vectors expressing murine factor VIII result in sustained correction of hemophilia A mice, Human Gene Therapy 14:143-152.

Maione et al., 1990, Inhibition of angiogenesis by recombinant human platelet factor-4 and related peptides, Science 247:77-79.

Mannino et al., 1988, Liposome mediated gene transfer, BioTechn. 6(7):682-690.

McCormick et al., 2003, Individualized human scFv vaccines produced in plants: humoral anti-idiotype responses in vaccinated mice confirm relevance to the tumor Ig, J. Immunol. Meth. 278:95-104.

Mendez et al., 1997, Functional transplant of megabase human immunoglobulin loci recapitulates human antibody response in mice, Nat. Gen. 15:146-156.

Miller, 1992, Human gene therapy comes of age, Nature 357:455-460.

Mulligan et al., 1980, Expression of a bacterial gene in mammalian cells, Science 209:1422-1427.

Nakai et al., 1998, Adeno-associated viral vector-mediated gene transfer of human blood coagulation factor IX into mouse liver, Blood 91(12):4600-4607.

Needleman et al., 1970, A general method applicable to the search for similarities in the amino acid sequence of two proteins, J. Mol. Biol. 48:443-453.

Niwa et al., 1991, Efficient selection for high-expression transfectants with a novel eukaryotic vector, Gene 108(2):193-199.

No et al., 1996, Ecdysone-inducible gene expression in mammalian cells and transgenic mice, Proc. Natl. Acad. Sci. USA 93:3346-3351.

Noel et al., 2002, High in vivo production of a model monoclonal antibody on adenoviral gene transfer, Human Gene Therapy 13:1483-1493.

O'Rourke et al., 2002, Comparison of gene transfer efficiencies and gene expression levels achieved with equine infectious anemia virus- and human immunodeficiency virus type 1-derived lentivirus vectors, J. Virol. 76(3):1510-1515.

Oh et al., 1992, Homeotic gene Antennapedia mRNA contains 5'-noncoding sequences that confer translational initiation by internal ribosome binding Gene & Dev. 6:1643-1653.

Ory et al., 1996, A stable human-derived packaging cell line for production of high titer retrovirus/vesicular stomatitis virus G pseudotypes, Proc. Natl. Acad. Sci. USA 93:11400-11406.

Osterberg et al., 2001, B-domain deleted recombinant factor VIII formulation and stability, Semin Hematol. 38(2 Suppl 4):40-3.

Osterwalder et al., 2001, A conditional tissue-specific transgene expression system using inducible GAL4, Proc. Natl. Acad. Sci. USA 98(22):12596-601.

Palmenberg, 1990, Proteolytic processing of picornaviral polyprotein, Ann. Rev. Microbiol. 44:603-623.

Paulus, 1998, Protein splicing: A novel form of gene expression and paradigm for self-catalyzed protein rearrangements, Pure & Appl. Chem. 70(1):1-8.

Pearson et al., 1988, Improved tools for biological sequence comparison, Proc. Natl. Acad. Sci. USA, 85:2444-2448.

Perollet, 1998, Platelet factor 4 modulates fibroblast growth factor 2 (FGF-2) activity and inhibits FGF-2 dimerization, Blood 91:3289-32-99.

Pittman et al., 1993, Biochemical, immunological, and in vivo functional characterization of B-domain-deleted factor VIII, Blood 81:2925-2935.

Pogue et al., 2002, Making an ally from an enemy: plant virology and the new agriculture, Ann .Rev. Phytopathol. 40:45-74.

Pollack et al., 1999, Transgenic milk as a method for the production of recombinant antibodies, J. Immunol. Meth. 231:147-157.

Rivera et al., 1996, A humanized system for pharmacologic control of gene expression,Nature Med. 2(9):1028-1032.

Roosien et al., 1990, Synthesis of foot-and-mouth disease virus capsid proteins in insect cells using baculovirus expression vectors, J. Gen. Virol 71:1703-1711.

Ryan et al., 1989, Specificity of enzyme-substrate interactions in foot-and-mouth disease virus polyprotein processing, Virology 173:35-45.

Ryan et al., 1991, Cleavage of foot-and-mouth disease virus polyprotein is mediated by residues located within a 19 amino acid sequence, J. Gen Virol. 72:2727-2732.

Ryan et al., 1994, Foot-and-mouth disease virus 2A oligopeptide mediated cleavage of an artificial polyprotein, The EMBO J. 15:928-933.

Sandberg et al., 2001, Structural and functional characterization of B-domain deleted recombinant factor VIII, Semin. Hematol. 38(2 Suppl 4):4-12.

Schillberg et al., 2003, Molecular farming of recombinant antibodies in plants, Cell Mol. Life Sci. 60(3):433-35.

Sharpe et al., 1990, Growth inhibition of *murine melanoma* and human colon carcinoma by recombinant human platelet factor 4, J. Natl. Cancer Inst. 82:848-853.

Shigekawa et al., 1988, Electroporation of eukaryotes and prokaryotes: a general approach to the introduction of macromolecules into cells, BioTechn. 6(8):742-751.

Smith et al., 1981, Comparison of biosequences, Adv. Appl. Math. 2:482-489.

Southern et al., 1982, Transformation of mammalian cells to antibiotic resistance with a bacterial gene under control of the SV40 early region promoter, J. Mol. Appl. Genet. 1(4):327-341.

Stein et al., 1998, Translation of vascular endothelial growth factor mRNA by internal ribosome entry: implications for translation under hypoxia, Mol. Cell. Biol. 18(6):3112-3119.

Streatfield et al., 2003, Plant-based vaccines, Int. J. Parasitol. 33:479-93.

Sugden et al., 1985, A vector that replicates as a plasmid and can be efficiently selected in B-lymphoblasts transformed by Epstein-Barr virus, Mol. Cell Biol. 5(2):410-413.

Suhr et al., 1998, High level transactivation by a modified *Bombyx* ecdysone receptor in mammalian cells without exogenous retinoid X receptor, Proc. Natl. Acad. Sci. USA 95:7999-8004.

Takahashi et al., 1993, A mutation of furin causes the lack of precursor-processing activity in human colon carcinoma LoVo cells, Biochem. Biophys. Res. Comm. 195:1019-26.

Tanaka et al., 1997, Viral vector-mediated transduction of a modified platelet factor 4 cDNA inhibits angiogenesis and tumor growth,Nat. Med. 3(4):437-442.

Teerink et al., 1995, The human insulin-like growth factor II leader 1 contains an internal ribosomal entry site, Biochim Biophys. Acta 1264:403-408.

Thompson, 2003, Structure and function of the factor VIII gene and protein, Semin. Thromb. Hemost. 29(1):11-22.

Torrent et al., 1996, Stable MLV-VL30 dicistronic retroviral vectors with a VL30 or MoMLV sequence promoting both packaging of genomic RNA and expression of the 3' cistron, Hum. Gene Ther. 7:603-612.

Tsukiyama-Kohara et al, 1992, Internal ribosome entry site within hepatitis C virus RNA, J. Virol. 66(3):1476-1483.

Vagner et al., 1995, Alternative translation of human fibroblast growth factor 2 mRNA occurs by internal entry of ribosomes, Mol. Cell Biol. 15(1):35-44.

Vakharia et al., 1987, Proteolytic processing of foot-and-mouth disease virus polyproteins expressed in a cell—free system from clone-derived transcripts, J. Gen. Virol 61:3199-3207.

Van der Velden et al., 1999, The role of the 5' untranslated region of an mRNA in translation regulation during development, Int. J. Biochem & Cell Bio. 31:87-106.

Vandendriessche et al., 2003, Gene therapy for the hemophilias, J. Thromb. Haemost. 1:1550-1558.

Witte et al., 1998, Monoclonal antibodies targeting the VEGF receptor-2 (Flk1/KDR) as an anti-angiogenic therapeutic strategy, Cancer Metastasis 17:155-161.

Xu et al., 2001, Optimization of transcriptional regulatory elements for constructing plasmid vectors, Gene 272:149-156.

Ye et al., 1999, Regulated delivery of therapeutic proteins after in vivo somatic cell gene transfer, Science 283:88-91.

Yonemura et al., 1993, Efficient production of recombinant human factor VIII by co-expression of the heavy and light chains, Protein Eng. 6:669-674.

Young et al., 1998, Production of recombinant antibodies in the milk of transgenic animals, Res. Immunol. 149(6):609-610.

Zhang et al., 1999, High levels of foreign gene expression in hepatocytes after tail vein injections of naked plasmid DNA, Human Gene Ther. 10:1735-1737.

Zufferey et al., 1997, Multiply attenuated lentiviral vector achieves efficient gene delivery in vivo, Nat. Biotech. 15:871-875.

Zufferey et al., 1998, Self-inactivating lentivirus vector for safe and efficient in vivo gene delivery, J. Virol. 72(12):9873-9880.

Li et al., A hepatocellular carcinoma-specific adenovirus variant, CV890, eliminates distant human liver tumors in combination with doxorubicin, Cancer Res. 61:6428-6436 (2001).

Collet et al., A binary plasmid system for shuffling combinatorial antibody libraries, Proc. Natl. Acad. Sci. USA 89:10026-10030 (1992).

Loiler et al., Targeting recombinant adeno-associated virus vectors to enhance gene transfer to pancreatic islets and liver, Gene Therapy 10:1551-1558 (2003).

Auricchio et al., "Pharmacological Regulation of Protein Expression from Adeno-Associated Viral Vectors in the Eye," *Mol. Ther.*, 6:238-242 (2002).

Bossis and Chiorini, "Cloning of an Avian-Associated Virus (AAAV) and Generation of Recombinant AAAV Particles," *J. Virol.*, 77:6799-68 10 (2003).

Burton et al., "Coexpression of Factor VIII Heavy and Light Chain Adeno-Associated Viral Vectors Produces Biologically Active Protein," *PNAS*, 96:12725-12730 (1999).

Costa et al., "The Cell-Specific Enhancer of the Mouse Transthyretin (Prealbumin) Gene Binds a Common Factor at One Site and a Liver-Specific Factor(s) at Two Other Sites," *Mol. Cell Biol.*, 8:81-90 (1988).

Davidson et al., "Recombinant Adeno-Associated Virus type 2, 4, and 5 Vectors: Transduction of Variant Cell Types and Regions in the Mammalian Central Nervous System," *PNAS USA*, 97:3428-32 (2000).

Galanis et al., "Phase II Trial of Temsirolimus (CCI-779) in Recurrent Glioblastoma Multiforme: A North Central Cancer Treatment Group Study," *J. Clin. Oncol*,. 23:5294-5304 (2005).

Gao et al., "Novel Adeno-Associated Viruses from Rhesus Monkeys as Vectors for Human Gene Therapy," *PNAS USA*, 99: 11854-11859 (2002).

Gao et al., "Adeno-Associated Viruses Undergo Substantial Evolution in Primates During Natural Infections," *PNAS USA*, 100:6081-6086 (2003).

McCarty et al., "Self-Complementary Recombinant Adeno-Associated Virus (scAAV) Vectors Promote Efficient Transduction Independently of DNA Synthesis," *Gene Ther.*, 8:1248-1254 (2001).

Passini et al., "Intraventricular Brain Injection of Adeno-Associated Virus Type 1 (AAV1) in Neonatal Mice Results in Complementary Patterns of Neuronal Transduction to AAV2 and total Long-Term Correction of Storage Lesions in the Brains of β-Glucuronidase-Deficient Mice," *J. Virol.*, 77:7034-7040 (2003).

Plate et al., "Vascular Endothelial Growth Factor is a Potential Tumour Angiogenesis Factor in Human Gliomas in Vivo," *Nature*, 359:845-848 (1992).

Rivera et al., "Long-Term Pharmacologically Regulated Expression of Erythropoietin in Primates following AAV-mediated gene transfer," *Blood*, 105:1424-1430 (2005).

Rivera et al., "Long-Term Regulated Expression of Growth Hormone in Mice after Intramuscular Gene Transfer," *PNAS USA*, 96:8657-8662 (1999).

Szymczak et al., "Correction of multi-gene deficiency in vivo using a single 'self-cleaving' 2A peptide-based retroviral vector," *Nat. Biotechnology.*, 22:589-599 (2004).

Ye et al., "Regulated Delivery of Therapeutic Proteins After in Vivo Somatic Cell Gene Transfer," *Science*, 283:88-91 (2000).

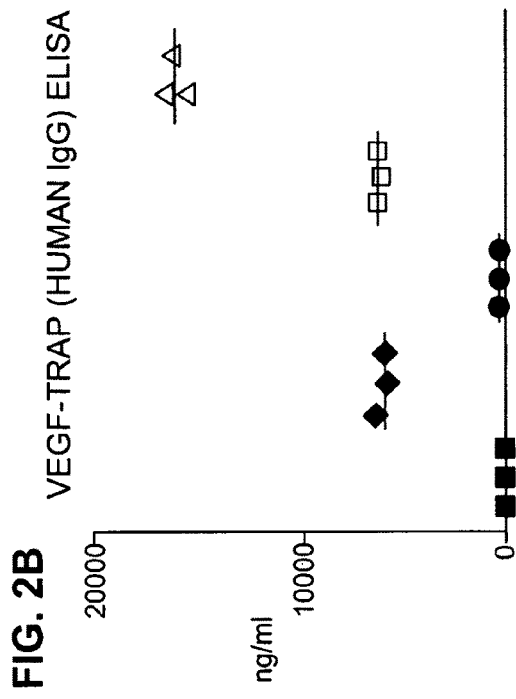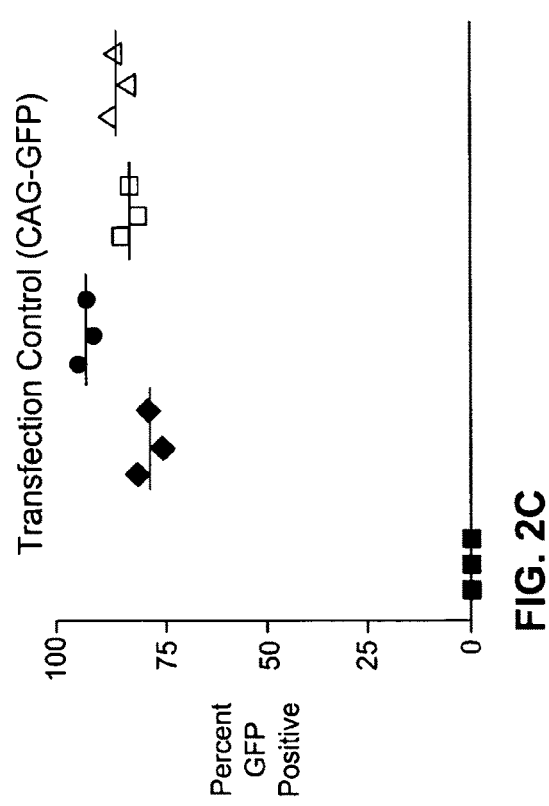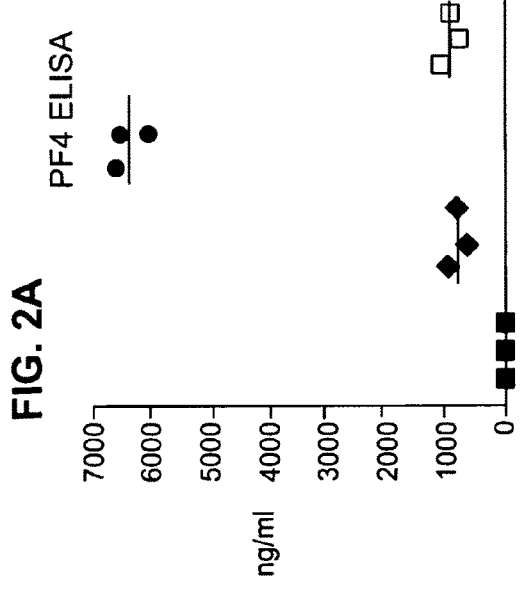

Heavy Chain EPRSFSQN — R740 Thrombin

BDD

Light Chain PPVLKRHQREITRT — R1648 Furin

D1 (SEQ ID NO: 39) EPRSFSQN — RAKR — 2A — SS — PPVLKRHQREITRT

D2 (SEQ ID NO: 40) EPRSFSQN — RAKR — 2A — SS — EITRT

E1 (SEQ ID NO: 41) EP — RAKR — 2A — SS — PPVLKRHQREIT

```
                              SEQUENCE LISTING

<160> NUMBER OF SEQ ID NOS: 42

<210> SEQ ID NO 1
    <211> LENGTH: 19
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 1

Leu Leu Asn Phe Asp Leu Leu Lys Leu Ala Gly Asp Val Glu Ser Asn
    1               5                   10                  15

Pro Gly Pro

<210> SEQ ID NO 2
    <211> LENGTH: 19
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 2

Thr Leu Asn Phe Asp Leu Leu Lys Leu Ala Gly Asp Val Glu Ser Asn
    1               5                   10                  15

Pro Gly Pro

<210> SEQ ID NO 3
    <211> LENGTH: 14
    <212> TYPE: PRT
    <213> ORGANISM: Artificial Sequence
    <220> FEATURE:
    <223> OTHER INFORMATION: Description of Artificial Sequence: Synthetic
          peptide
```

```
<400> SEQUENCE: 3

Leu Leu Lys Leu Ala Gly Asp Val Glu Ser Asn Pro Gly Pro
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Phe Asp Leu Leu Lys Leu Ala Gly Asp Val Glu Ser Asn Pro Gly
1               5                   10                  15

Pro

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Leu Leu Asn Phe Asp Leu Leu Lys Leu Ala Gly Asp Val Glu Ser
1               5                   10                  15

Asn Pro Gly Pro
            20

<210> SEQ ID NO 6
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 7
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr Leu Asn Phe Asp Leu Leu Lys Leu
        35                  40                  45

Ala Gly Asp Val Glu Ser Asn Pro Gly Pro
        50                  55
```

```
<210> SEQ ID NO 8
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 9
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Lys or Arg

<400> SEQUENCE: 10

Arg Xaa Xaa Arg
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu or Asp

<400> SEQUENCE: 11

Ile Xaa Gly Arg
1
```

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Ala Gly Phe Ala Thr Val Ala Gln Ala
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Val Pro Arg Gly Ser
1               5

<210> SEQ ID NO 14
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gctccagtaa agcagactct aaacttcgat cttctcaagc tcgctggaga tgttgagagc      60
aacccaggtc ca                                                          72

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agagctaaga gg                                                          12

<210> SEQ ID NO 16
<211> LENGTH: 593
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aaccccccact    240 ggttggggca ttgccaccac ctgtcagctc ctttccggga ctttcgcttt ccccctccct     300
attgccacgg cggaactcat cgccgcctgc cttgcccgct gctggacagg gctcggctg      360 ttgggcactg acaattccgt ggtgttgtcg gggaagctga cgtcctttcc atggctgctc     420

-continued

```
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tgg           593
```

<210> SEQ ID NO 17
<211> LENGTH: 224
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gtgagatccg ctcgctgatc agcctcgact gtgccttcta gttgccagcc atctgttgtt    60
tgcccctccc ccgtgccttc cttgaccctg aaggtgccac tcccactgt cctttcctaa    120 taaaatgagg aaattgcatc gcattgtctg agtaggtgtc attctattct gggggtggg    180 gtggggcagg acagcaaggg ggaggattgg aagacaata gcag                     224
```

<210> SEQ ID NO 18
<211> LENGTH: 492
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
gttattttcc accatattgc cgtcttttgg caatgtgagg gcccggaaac ctggccctgt    60
cttcttgacg agcattccta ggggtctttc ccctctcgcc aaaggaatgc aaggtctgtt    120
gaatgtcgtg aaggaagcag ttcctctgga agcttcttga agacaaacaa cgtctgtagc    180 gacccttttgc aggcagcgga accccccacc tggcgacagg tgcctctgcg gccaaaagcc    240
acgtgtataa gatacacctg caaaggcggc acaaccccag tgccacgttg tgagttggat    300
agttgtggaa agagtcaaat ggctctcctc aagcgtattc aacaagggc tgaaggatgc    360 ccagaaggta ccccattgta tgggatctga tctggggcct cggtgcacat gctttacatg    420
tgtttagtcg aggttaaaaa aacgtctagg cccccgaac cacggggacg tggttttcct    480
ttgaaaaaca cg                                                       492
```

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
ggaaaatttg cttggacctg cgagccccgc tgtacaagaa aataattaag              50
```

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
cttaattatt ttcttgtaca gcggggctcg caggtccaag caaatttcc                50
```

```
<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gactagcagt ccggaggtag acctttcgta gagatg                              36

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cggactcaga accacatcta tgattgtatt ggt                                 33

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acaatcatag atgtggttct gagtccgtct catgcccact gtgc                     44

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gataatgccc gggccctttt catggaccct gacaaatg                            38

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agggcccggg cgacaaaact cacacatgcc cactgtgc                            38

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cattcgctag caatt                                                     15
```

<210> SEQ ID NO 27
<211> LENGTH: 93
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tcgaagatct atggtcagct actgggacac cggggtcctg ctgtgcgcgc tgctcagctg    60
tctgcttctc acaggatcta gttccggagg tag                                93

<210> SEQ ID NO 28
<211> LENGTH: 93
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctacctccgg aactagatcc tgtgagaagc agacagctga gcagcgcgca cagcaggacc    60
ccggtgtccc agtagctgac ctaagatctt cga                                93

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
actggagccc tcttagctct actctccaaa agtttcttaa                          40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
actggagccc tcttagctct actctccaaa agtttcttaa                          40

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttgagagcaa cccaggtcca atggtcagct actgggacac                          40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtgtcccagt agctgaccat tggacctggg ttgctctcaa         40

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttcctcgaag atctaggctg         20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cttatgctga tgcttcgaag         20

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atagatctcg tgtttttcaa aggaaaacca cg         32

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgaccggtcg tgtttttcaa aggaaaacca cg         32

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
attgcggccg cgttatttc caccatattg c         31

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 38

Arg Ala Lys Arg
1

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Pro Arg Ser Phe Ser Gln Asn
1               5

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Pro Val Leu Lys Arg His Gln Arg Glu Ile Thr Arg Thr
1               5                   10

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Ile Thr Arg Thr
1               5

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Leu Ser His Ser Pro Gly Lys Arg Ala
1               5                   10
```

COMPOSITIONS AND METHODS FOR ENHANCED EXPRESSION OF RECOMBINANT POLYPEPTIDES FROM A SINGLE VECTOR USING A PEPTIDE CLEAVAGE SITE

CROSS-REFERENCE TO RELATED APPLICATIONS

This application is a continuation of co-pending U.S. patent application Ser. No. 10/831,304, filed Apr. 26, 2004, which claims the priority benefit of U.S. patent application Ser. No. 10/452,253, filed Jun. 3, 2003, now U.S. Pat. No. 7,485,291, and U.S. Provisional Patent Application No. 60/540,553, filed Feb. 2, 2004. Each of these applications is hereby incorporated by reference herein in their entirety.

The sequence Listing for this application is submitted as a text file via EFS-Web, and is incorporated by reference herein. The name of the text file containing the Sequence Listing is sequence.txt. The text file is 13025 bytes (12.7 KB), and was created on Jul. 21, 2009.

FIELD OF THE INVENTION

The invention relates to novel vector or plasmid constructs designed to express recombinant polypeptides or fragments thereof by using a self-processing peptide. The constructs may be used for in vitro, ex vivo or in vivo delivery of heterologous protein or polypeptide coding sequences to a cell, or in the production of recombinant polypeptides by vector-transduced or plasmid transfected cells.

BACKGROUND OF THE INVENTION

Recombinant proteins as therapeutic modalities have found increasing use in recent years. Numerous recombinant protein-based therapies are in various stages of clinical development. One limitation to widespread clinical application of recombinant protein technology is the difficulty in production of proteins that include two or more coding sequences or domains such that the domains are expressed in the proper ratio with appropriate post-translational processing resulting in production of a functional heterodimeric molecule. A further limitation is the high cost associated with adequate levels of expression for clinical applications.

Chinese Hamster Ovarian (CHO) cells are the most commonly used mammalian cell lines for commercial scale production of glycosylated human proteins. Previous attempts to express a full length recombinant protein with two or more domains or chains (and thus two or more coding sequences or open reading frames (ORFs)) via recombinant DNA technology using a single vector have met with limited success, typically resulting in unequal levels of expression of the two or more domains or chains of the protein or polypeptide and more particularly, a lower level of expression for the second coding sequence. In order to express a fully biological functional protein or polypeptide which has two or more domains or chains from a single vector, equimolar expression of the two or more domains or chains is typically required. Additionally, conventional vectors relying on dual promoter regulation of gene expression are invariably affected by promoter interaction (i.e., promoter interference) which may compromise equimolar or substantially equimolar expression of the genes. Other factors that limit the ability to express two or more coding sequences from a single vector include the packaging limitation of the vector itself. For example, in considering the appropriate vector/coding sequence combination, factors to be considered include: the capacity of the vector (e.g., approx. 4,500 bp for AAV); the duration of expression of the recombinant molecule by vector-transduced cells (e.g., short term expression for adenoviral vectors); the cell types infected by the vector if a viral vector is used; and the desired expression level of the target gene product(s). The requirement for controlled expression of two or more gene products together with the packaging limitations of viral vectors such as adenovirus and AAV restrict the choices with respect to vector construction and systems for expression of a protein or polypeptide which has two or more domains or chains.

The linking of proteins in the form of polyproteins in a single open reading frame is a strategy adopted in the replication of many viruses including picornaviridae. Upon translation, virus-encoded proteinases mediate rapid intramolecular (cis) cleavage of a polyprotein to yield discrete mature protein products. Foot and Mouth Disease viruses (FMDV) are a group within the picornaviridae which express a single, long open reading frame encoding a polyprotein of approximately 225 kD. The full length translation product undergoes rapid intramolecular (cis) cleavage at the C-terminus of a self-processing cleavage site, for example, a 2A site or region, located between the capsid protein precursor (P1-2A) and replicative domains of the polyprotein 2BC and P3, with the cleavage mediated by proteinase-like activity of the 2A region itself (Ryan et al., J. Gen. Virol. 72:2727-2732, 1991); Vakharia et al., J. Virol. 61:3199-3207, 1987). Similar domains have also been characterized from aphthoviridea and cardioviridae of the picornavirus family (Donnelly et al., J. Gen. Virol. 78:13-21, 1997).

In order to express proteins or polypeptides which have two or more domains or chains from a single vector, two or more promoters or an internal ribosome entry site (IRES) sequence are generally used to drive expression of individual genes. The use of two promoters within a single vector can result in low protein expression, e.g., due to promoter interference. When two genes are linked with an IRES sequence, the expression level of the second gene is often significantly lower than the first gene (Furler et al., Gene Therapy 8:864-873, 2001).

There remains a need for improved gene expression systems for production of recombinant proteins and polypeptides, in particular proteins and polypeptides that have two or more domains or chains, such that sufficient expression of a biologically active recombinant protein or polypeptide is achieved at commercially reasonable cost.

The present invention addresses this need by demonstrating the feasibility and use of a single vector or plasmid construct comprising a sequence that encodes a self-processing peptide which results in the expression of functional recombinant proteins and polypeptides.

SUMMARY OF THE INVENTION

The present invention provides a means for recombinant protein or polypeptide expression using a self-processing peptide which facilitates efficient expression of two or more polypeptides from a single open reading frame by providing a "cleavage" site to generate individual polypeptides.

The present invention provides a system for expression of a protein or polypeptide based on substantially equal expression of the coding sequence for two or more proteins or polypeptides or domains or chains thereof under transcriptional control of the same promoter from a single vector, wherein translation is mediated by a self-processing cleavage site, e.g., a 2A or 2A-like sequence.

In one preferred aspect, the invention provides a vector or construct for expression of two or more recombinant proteins or polypeptides or a recombinant protein or polypeptide which has two or more domains or chains (and thus two or more coding sequences or open reading frames (ORFs)). In an exemplary construct wherein 2 coding sequences are expressed, the vector includes in the 5' to 3' direction: a promoter operably linked to the coding sequence for a first protein or polypeptide ORF, a sequence encoding a self-processing cleavage site and the coding sequence for a second protein or polypeptide ORF, wherein the sequence encoding the self-processing cleavage site is inserted between the coding sequence for the first protein or polypeptide and the coding sequence for the second protein or polypeptide.

The vector may be any recombinant vector capable of expression of a protein or polypeptide of interest or a fragment thereof, for example, an adeno-associated virus (AAV) vector, a lentivirus vector, a retrovirus vector, a replication competent adenovirus vector, a replication deficient adenovirus vector (e.g., a gutless adenovirus vector), a herpes virus vector, a baculovirus vector or a nonviral plasmid.

Preferred self-processing cleavage sequences include a 2A sequence, e.g., a 2A sequence derived from Foot and Mouth Disease Virus (FMDV).

In a further preferred aspect, the vector comprises a sequence which encodes an additional proteolytic cleavage site located between the coding sequence for a first chain of a protein or polypeptide and the coding sequence for a second chain of a protein or polypeptide, e.g., a furin cleavage site with the consensus sequence RXK(R)R (presented as SEQ ID NO:10).

A vector for recombinant protein or polypeptide expression using a self-processing peptide may include any of a number of promoters, wherein the promoter is constitutive, regulatable or inducible, cell type specific, tissue-specific, or species specific.

The vector may further comprise a signal sequence for the coding sequence of a domain of the protein or polypeptide.

In one preferred aspect of the invention, two or more protein or polypeptide coding sequences are expressed in a substantially equimolar ratio.

The invention further provides host cells transduced with a vector or plasmid that comprises that comprises a sequence encoding a self-processing cleavage site alone or in combination with a sequence encoding an additional proteolytic cleavage site and use of such cells in generating recombinant proteins or polypeptides.

In a related aspect, the invention provides a recombinant protein or polypeptide produced by such a cell and methods for producing the same.

Other and further objects, features and advantages are apparent from the following description of the embodiments for the invention given the purpose of disclosure when taken in conjunction with the accompanying drawings.

BRIEF DESCRIPTION OF THE DRAWINGS

FIGS. 2A-C show expression levels of VEGF-TRAP and sPF4 from plasmids expressing both proteins from a single promoter using F2A and IRES sequences, where FIG. 2A illustrates the level of PF4 produced as analyzed by ELISA (ng/ml); FIG. 2B illustrates the level of VEGF TRAP produced as analyzed by ELISA (ng/ml); and FIG. 2C illustrates the expression level of the GFP transfection control indicated as percent positive.

FIG. 4 (SEQ ID NOS: 38-41) depicts an expression cassette for expression of two polypeptides (Factor VIII heavy and light chains), wherein various sequences for B domain deleted forms of Factor VIII are presented.

FIG. 9A shows the results of PAGE using a 12% native gel and FIG. 9B shows the results of PAGE using a 12% reducing gel wherein Lane 1 shows IgG produced from a hybridoma; Lane 2 shows IgG expressed using a 2A sequence in 293T cells and Lane 3 is a 293T mock control.

DETAILED DESCRIPTION OF THE INVENTION

Figure 1A:
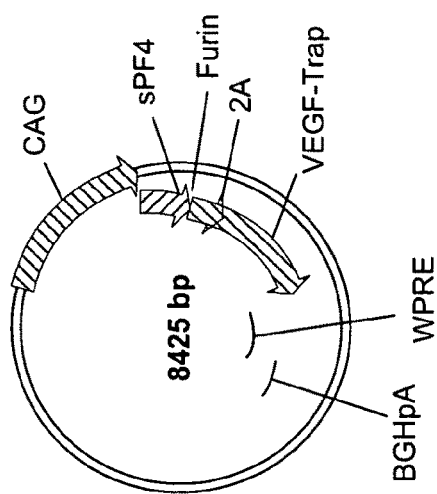
FIGS. 1A-D depict exemplary plasmids for the expression of soluble platelet factor 4 (sPF4) and VEGF TRAP wherein the plasmids comprise the coding sequences and either a F2A sequence or an IRES in alternate orientations as described in Example 1. The figures illustrate plasmids comprising in the 5' to 3' direction: sPF4:F2A:VEGF TRAP (FIG. 1A); sPF4: EMCV IRES:VEGF TRAP (FIG. 1B); VEGF TRAP:F2A: sPF4 (FIG. 1C); VEGF TRAP:EMCV IRES:sPF4 (FIG. 1D)
Figure 1B:
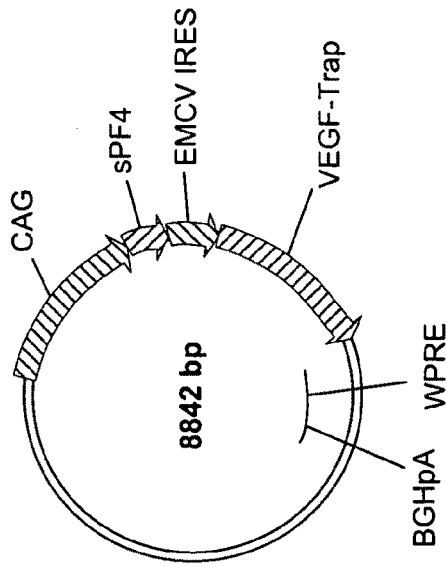
Figure 1C:
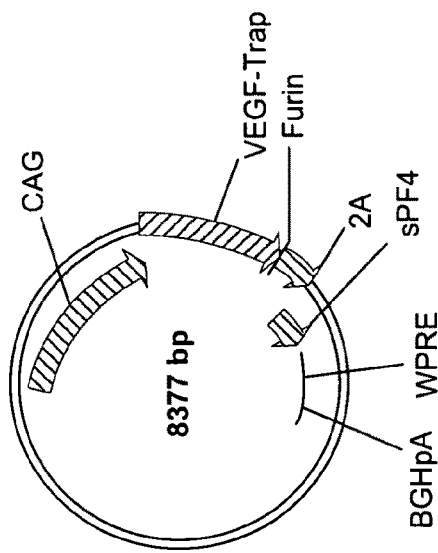
Figure 1D:
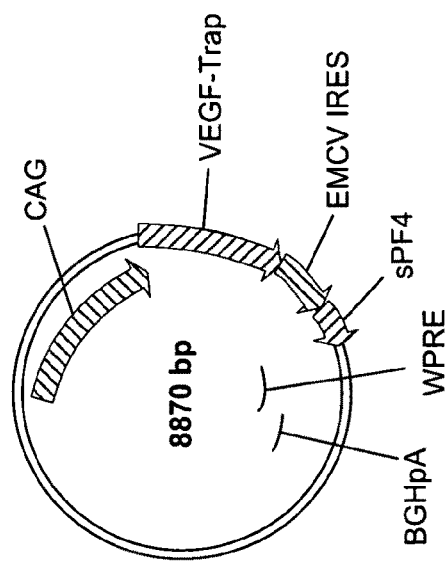

The present invention provides single vector or plasmid constructs for expression of two or more protein or polypeptide open reading frames and methods of using the same. The vectors have a self-processing cleavage sequence between the protein or polypeptide coding sequences allowing for expression of more than one functional protein or polypeptide using a single promoter. The invention finds utility in production of two or more proteins or polypeptides or a protein or polypeptide having two or more domains (or chains) using a single vector where expression occurs under operative control of a single promoter. Exemplary vector constructs comprise a self-processing cleavage sequence and may further comprise an additional proteolytic cleavage site for removal of the self-processing cleavage sequence from the expressed protein or polypeptide. The vector constructs find utility in methods relating to enhanced production of biologically active proteins, polypeptides or fragments thereof in vitro and in vivo.

The various compositions and methods of the invention are described below. Although particular compositions and methods are exemplified herein, it is understood that any of a number of alternative compositions and methods are applicable and suitable for use in practicing the invention. It will also be understood that an evaluation of the protein or polypeptide expression constructs (vectors) and methods of the invention may be carried out using procedures standard in the art.

The practice of the present invention will employ, unless otherwise indicated, conventional techniques of cell biology, molecular biology (including recombinant techniques), microbiology, biochemistry and immunology, which are known to those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

DEFINITIONS

Unless otherwise indicated, all terms used herein have the same meaning as they would to one skilled in the art and the practice of the present invention will employ, conventional techniques of microbiology and recombinant DNA technology, which are within the knowledge of those of skill of the art.

The term "vector", as used herein, refers to a DNA or RNA molecule such as a plasmid, virus or other vehicle, which contains one or more heterologous or recombinant DNA sequences and is designed for transfer between different host cells. The terms "expression vector" and "gene therapy vector" refer to any vector that is effective to incorporate and express heterologous DNA fragments in a cell. A cloning or expression vector may comprise additional elements, for example, the expression vector may have two replication systems, thus allowing it to be maintained in two organisms, for example in human cells for expression and in a prokaryotic host for cloning and amplification. Any suitable vector can be employed that is effective for introduction of nucleic acids into cells such that protein or polypeptide expression results, e.g. a viral vector or non-viral plasmid vector. Any cells effective for expression, e.g., insect cells and eukaryotic cells such as yeast or mammalian cells are useful in practicing the invention.

The terms "heterologous DNA" and "heterologous RNA" refer to nucleotides that are not endogenous (native) to the cell or part of the genome in which they are present. Generally heterologous DNA or RNA is added to a cell by transduction, infection, transfection, transformation or the like, as further described below. Such nucleotides generally include at least one coding sequence, but the coding sequence need not be expressed. The term "heterologous DNA" may refer to a "heterologous coding sequence" or a "transgene".

As used herein, the terms "protein" and "polypeptide" may be used interchangeably and typically refer to "proteins" and "polypeptides" of interest that are expresses using the self processing cleavage site-containing vectors of the present invention. Such "proteins" and "polypeptides" may be any protein or polypeptide useful for research, diagnostic or therapeutic purposes, as further described below.

The term "replication defective" as used herein relative to a viral gene therapy vector of the invention means the viral vector cannot independently further replicate and package its genome. For example, when a cell of a subject is infected with rAAV virions, the heterologous gene is expressed in the infected cells, however, due to the fact that the infected cells lack AAV rep and cap genes and accessory function genes, the rAAV is not able to replicate.

As used herein, a "retroviral transfer vector" refers to an expression vector that comprises a nucleotide sequence that encodes a transgene and further comprises nucleotide sequences necessary for packaging of the vector. Preferably, the retroviral transfer vector also comprises the necessary sequences for expressing the transgene in cells.

As used herein, "packaging system" refers to a set of viral constructs comprising genes that encode viral proteins involved in packaging a recombinant virus. Typically, the constructs of the packaging system will ultimately be incorporated into a packaging cell.

As used herein, a "second generation" lentiviral vector system refers to a lentiviral packaging system that lacks functional accessory genes, such as one from which the accessory genes, vif, vpr, vpu and nef, have been deleted or inactivated. See, e.g., Zufferey et al., 1997, Nat. Biotechnol. 15:871-875.

As used herein, a "third generation" lentiviral vector system refers to a lentiviral packaging system that has the characteristics of a second generation vector system, and further lacks a functional tat gene, such as one from which the tat gene has been deleted or inactivated. Typically, the gene encoding rev is provided on a separate expression construct. See, e.g., Dull et al., 1998, J. Virol. 72(11):8463-8471.

As used herein, "pseudotyped" refers to the replacement of a native envelope protein with a heterologous or functionally modified envelope protein.

The term "operably linked" as used herein relative to a recombinant DNA construct or vector means nucleotide components of the recombinant DNA construct or vector are functionally related to one another for operative control of a selected coding sequence. Generally, "operably linked" DNA sequences are contiguous, and, in the case of a secretory leader, contiguous and in reading frame. However, enhancers do not have to be contiguous.

As used herein, the term "gene" or "coding sequence" means the nucleic acid sequence which is transcribed (DNA) and translated (mRNA) into a polypeptide in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

A "promoter" is a DNA sequence that directs the binding of RNA polymerase and thereby promotes RNA synthesis, i.e., a minimal sequence sufficient to direct transcription. Promoters and corresponding protein or polypeptide expression may be cell-type specific, tissue-specific, or species specific. Also included in the nucleic acid constructs or vectors of the invention are enhancer sequences which may or may not be contiguous with the promoter sequence. Enhancer sequences influence promoter-dependent gene expression and may be located in the 5' or 3' regions of the native gene.

"Enhancers" are cis-acting elements that stimulate or inhibit transcription of adjacent genes. An enhancer that inhibits transcription also is termed a "silencer". Enhancers can function (i.e., can be associated with a coding sequence) in either orientation, over distances of up to several kilobase pairs (kb) from the coding sequence and from a position downstream of a transcribed region.

A "regulatable promoter" is any promoter whose activity is affected by a cis or trans acting factor (e.g., an inducible promoter, such as an external signal or agent).

A "constitutive promoter" is any promoter that directs RNA production in many or all tissue/cell types at most times, e.g., the human CMV immediate early enhancer/promoter region which promotes constitutive expression of cloned DNA inserts in mammalian cells.

The terms "transcriptional regulatory protein", "transcriptional regulatory factor" and "transcription factor" are used interchangeably herein, and refer to a nuclear protein that binds a DNA response element and thereby transcriptionally regulates the expression of an associated gene or genes. Transcriptional regulatory proteins generally bind directly to a DNA response element, however in some cases binding to DNA may be indirect by way of binding to another protein that in turn binds to, or is bound to a DNA response element.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson R J, Howell M T, Kaminski A (1990) Trends Biochem Sci 15(12):477-83) and Jackson R J and Kaminski, A. (1995) RNA 1(10):985-1000. The examples described herein are relevant to the use of any IRES element, which is able to promote direct internal ribosome entry to the initiation codon of a cistron. "Under translational control of an IRES" as used herein means that translation is associated with the IRES and proceeds in a cap-independent manner.

A "self-processing cleavage site" or "self-processing cleavage sequence" is defined herein as a post-translational or co-translational processing cleavage site sequence. Such a "self-processing cleavage" site or sequence refers to a DNA or amino acid sequence, exemplified herein by a 2A site, sequence or domain or a 2A-like site, sequence or domain. As used herein, a "self-processing peptide" is defined herein as the peptide expression product of the DNA sequence that encodes a self-processing cleavage site or sequence, which upon translation, mediates rapid intramolecular (cis) cleavage of a protein or polypeptide comprising the self-processing cleavage site to yield discrete mature protein or polypeptide products.

As used herein, the term "additional proteolytic cleavage site", refers to a sequence which is incorporated into an expression construct of the invention adjacent a self-processing cleavage site, such as a 2A or 2A like sequence, and provides a means to remove additional amino acids that remain following cleavage by the self processing cleavage sequence. Exemplary "additional proteolytic cleavage sites" are described herein and include, but are not limited to, furin cleavage sites with the consensus sequence RXK(R)R (SEQ ID NO: 10). Such furin cleavage sites can be cleaved by endogenous subtilisin-like proteases, such as furin and other serine proteases within the protein secretion pathway.

As used herein, the terms "immunoglobulin" and "antibody" may be used interchangeably and refer to intact immunoglobulin or antibody molecules as well as fragments thereof, such as Fa, F(ab')2, and Fv, which are capable of binding an antigenic determinant. Such an "immunoglobulin" and "antibody" is composed of two identical light polypeptide chains of molecular weight approximately 23,000 daltons, and two identical heavy chains of molecular weight 53,000-70,000. The four chains are joined by disulfide bonds in a "Y" configuration. Heavy chains are classified as gamma (IgG), mu (IgM), alpha (IgA), delta (IgD) or epsilon (IgE) and are the basis for the class designations of immunoglobulins, which determines the effector function of a given antibody. Light chains are classified-as either kappa or lambda. When reference is made herein to an "immunoglobulin or fragment thereof", it will be understood that such a "fragment thereof" is an immunologically functional immunoglobulin fragment.

The term "humanized antibody" refers to an antibody molecule in which one or more amino acids of the antigen binding regions of a non-human antibody have been replaced in order to more closely resemble a human antibody, while retaining the binding activity of the original non-human antibody. See, e.g., U.S. Pat. No. 6,602,503.

The term "antigenic determinant", as used herein, refers to that fragment of a molecule (i.e., an epitope) which makes contact with a particular antibody. Numerous regions of a protein or fragment of a protein may induce the production of antibodies which binds specifically to a given region of the three-dimensional structure of the protein. These regions or structures are referred to as antigenic determinants. An antigenic determinant may compete with the intact antigen (i.e., the immunogen used to elicit the immune response) for binding to an antibody.

The term "fragment," when referring to a recombinant protein or polypeptide of the invention means a polypeptide which has an amino acid sequence which is the same as part of, but not all of, the amino acid sequence of the corresponding full length protein or polypeptide, which retains at least one of the functions or activities of the corresponding full length protein or polypeptide. The fragment preferably includes at least 20-100 contiguous amino acid residues of the full length protein or polypeptide.

The terms "administering" or "introducing", as used herein refer to delivery of a vector for recombinant protein expression to a cell or to cells and or organs of a subject. Such administering or introducing may take place in vivo, in vitro or ex vivo. A vector for recombinant protein or polypeptide expression may be introduced into a cell by transfection, which typically means insertion of heterologous DNA into a cell by physical means (e.g., calcium phosphate transfection, electroporation, microinjection or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage).

"Transformation" is typically used to refer to bacteria comprising heterologous DNA or cells which express an oncogene and have therefore been converted into a continuous growth mode such as tumor cells. A vector used to "transform" a cell may be a plasmid, virus or other vehicle.

Typically, a cell is referred to as "transduced", "infected", "transfected" or "transformed" dependent on the means used for administration, introduction or insertion of heterologous DNA (i.e., the vector) into the cell. The terms "transduced", "transfected" and "transformed" may be used interchangeably herein regardless of the method of introduction of heterologous DNA.

As used herein, the terms "stably transformed", "stably transfected" and "transgenic" refer to cells that have a non-native (heterologous) nucleic acid sequence integrated into the genome. Stable transfection is demonstrated by the establishment of cell lines or clones comprised of a population of daughter cells containing the transfected DNA stably integrated into their genomes. In some cases, "transfection" is not stable, i.e., it is transient. In the case of transient transfection, the exogenous or heterologous DNA is expressed, however, the introduced sequence is not integrated into the genome and is considered to be episomal.

As used herein, "ex vivo administration" refers to a process where primary cells are taken from a subject, a vector is administered to the cells to produce transduced, infected or transfected recombinant cells and the recombinant cells are readministered to the same or a different subject.

A "multicistronic transcript" refers to an mRNA molecule that contains more than one protein coding region, or cistron. A mRNA comprising two coding regions is denoted a "bicistronic transcript." The "5'-proximal" coding region or cistron is the coding region whose translation initiation codon (usually AUG) is closest to the 5'-end of a multicistronic mRNA molecule. A "5'-distal" coding region or cistron is one whose translation initiation codon (usually AUG) is not the closest initiation codon to the 5' end of the mRNA. The terms "5'-distal" and "downstream" are used synonymously to refer to coding regions that are not adjacent to the 5' end of a mRNA molecule.

As used herein, "co-transcribed" means that two (or more) coding regions or polynucleotides are under transcriptional control of a single transcriptional control or regulatory element.

The term "host cell", as used herein refers to a cell which has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

As used herein, the terms "biological activity" and "biologically active", refer to the activity attributed to a particular protein in a cell line in culture or in a cell-free system, such as a ligand-receptor assay in ELISA plates. The "biological activity" of an "immunoglobulin", "antibody" or fragment thereof refers to the ability to bind an antigenic determinant and thereby facilitate immunological function.

As used herein, the terms "tumor" and "cancer" refer to a cell that exhibits a loss of growth control and forms unusually large clones of cells. Tumor or cancer cells generally have lost contact inhibition and may be invasive and/or have the ability to metastasize.

Internal Ribosome Entry Site (IRES)

IRES elements were first discovered in picornavirus mRNAs (Jackson R J, Howell M T, Kaminski A (1990) *Trends Biochem Sci* 15(12):477-83) and Jackson R J and Kaminski, A. (1995) *RNA* 1(10):985-1000). Examples of IRES generally employed by those of skill in the art include those referenced in Table I, as well as those described in U.S. Pat. No. 6,692,736. Examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. (1998) Mol. Cell. Biol. 18(11):6178-6190), the fibroblast growth factor 2 (FGF-2), and insulin-like growth factor (IGFII), the translational initiation-factor eIF4G and yeast transcription factors TFIID and HAP4, the encephelomycarditis virus (EMCV) which is commercially available from Novagen (Duke et al. (1992) *J. Virol* 66(3):1602-9) and the VEGF IRES (Huez et al. (1998) *Mol Cell Biol* 18(11):6178-90). IRES have also been reported in different viruses such as cardiovirus, rhinovirus, aphthovirus, HCV, Friend murine leukemia virus (FrMLV) and Moloney murine leukemia virus (MoMLV). As used herein, "IRES" encompasses functional variations of IRES sequences as long as the variation is able to promote direct internal ribosome entry to the initiation codon of a cistron. An IRES may be mammalian, viral or protozoan.

The IRES promotes direct internal ribosome entry to the initiation codon of a downstream cistron, leading to cap-independent translation. Thus, the product of a downstream cistron can be expressed from a bicistronic (or multicistronic) mRNA, without requiring either cleavage of a polyprotein or generation of a monocistronic mRNA. Internal ribosome entry sites are approximately 450 nucleotides in length and are characterized by moderate conservation of primary sequence and strong conservation of secondary structure. The most significant primary sequence feature of the IRES is a pyrimidine-rich site whose start is located approximately 25 nucleotides upstream of the 3' end of the IRES. See Jackson et al. (1990).

Three major classes of picornavirus IRES have been identified and characterized: (1) the cardio- and aphthovirus class (for example, the encephelomycarditis virus, Jang et al. (1990) *Gene Dev* 4:1560-1572); (2) the entero- and rhinovirus class (for example, polioviruses, Borman et al. (1994) *EMBO J.* 13:314903157); and (3) the hepatitis A virus (HAV) class, Glass et al. (1993) *Virol* 193:842-852). For the first two classes, two general principles apply. First, most of the 450-nucleotide sequence of the IRES functions to maintain particular secondary and tertiary structures conducive to ribosome binding and translational initiation. Second, the ribosome entry site is an AUG triplet located at the 3' end of the IRES, approximately 25 nucleotides downstream of a conserved oligopyrimidine tract. Translation initiation can occur either at the ribosome entry site (cardioviruses) or at the next downstream AUG (entero/rhinovirus class). Initiation occurs at both sites in aphthoviruses.

HCV and pestiviruses such as bovine viral diarrhea virus (BVDV) or classical swine fever virus (CSFV) have 341 nt and 370 nt long 5'-UTR respectively. These 5'-UTR fragments form similar RNA secondary structures and can have moderately efficient IRES function (Tsukiyama-Kohara et al. (1992) *J. Virol.* 66:1476-1483; Frolov I et al., (1998) *RNA* 4:1418-1435). Recent studies showed that both Friend-murine leukemia virus (MLV) 5'-UTR and rat retrotransposon virus-like 30S (VL30) sequences contain IRES structure of retroviral origin (Torrent et al. (1996) *Hum Gene Ther* 7:603-612).

In eukaryotic cells, translation is normally initiated by the ribosome scanning from the capped mRNA 5' end, under the control of initiation factors. However, several cellular mRNAs have been found to have IRES structure to mediate the cap-independent translation (van der Velde, et al. (1999) *Int J Biochem Cell Biol.* 31:87-106). Examples are immunoglobulin heavy-chain binding protein (BiP) (Macejak et al.

(1991) *Nature* 353:90-94), antennapedia mRNA of Drosophilan (Oh et al. (1992) *Gene and Dev* 6:1643-1653), fibroblast growth factor-2 (FGF-2) (Vagner et al. (1995) *Mol Cell* moter. In addition, an IRES sequence may be sufficiently long to present issues with the packaging limit of the vector, e.g., the eCMV IRES has a length of 507 base pairs.

TABLE 1

LITERATURE REFERENCES FOR IRES

| IRES Host | Example | Reference |
|---|---|---|
| Picornavirus | HAV | Glass et al., 1993. Virol 193: 842-852 |
| | EMCV | Jang & Wimmer, 1990. Gene Dev 4: 1560-1572 |
| | Poliovirus | Borman et al., 1994. EMBO J 13: 3149-3157 |
| HCV and | HCV | Tsukiyama-Kohara et al., 1992. J Virol 66: 1476-1483 |
| pestivirus | BVDV | Frolov I et al., 1998. RNA. 4: 1418-1435 |
| Leishmania virus | LRV-1 | Maga et al., 1995. Mol Cell Biol 15: 4884-4889 |
| Retroviruses | MoMLV | Torrent et al., 1996. Hum Gene Ther 7: 603-612 |
| | VL30 (Harvey murine sarcoma virus) | |
| | REV | Lopez-Lastra et al., 1997. Hum Gene Ther 8: 1855-1865 |
| Eukaryotic | BiP | Macejak & Sarnow, 1991. Nature 353: 90-94 |
| mRNA | antennapedia mRNA | Oh et al., 1992. Gene & Dev 6: 1643-1653 |
| | FGF-2 | Vagner et al., 1995. Mol Cell Biol 15: 35-44 |
| | PDGF-B | Bernstein et al., 1997. J Biol Chem 272: 9356-9362 |
| | IGFII | Teerink et al., 1995. Biochim Biophys Acta 1264: 403-408 |
| | eIF4G | Gan & Rhoads, 1996. J Biol Chem 271: 623-626 |
| | VEGF | Stein et al., 1998. Mol Cell Biol 18: 3112-3119; Huez et al., 1998. Mol Cell Biol 18: 6178-6190 |

*Biol* 15:35-44), platelet-derived growth factor B (PDGF-B) (Bernstein et al. (1997) *J Biol Chem* 272:9356-9362), insulin-like growth factor II (Teerink et al. (1995) *Biochim Biophys Acta* 1264:403-408), and the translation initiation factor eIF4G (Gan et al. (1996) *J Biol Chem* 271:623-626). Recently, vascular endothelial growth factor (VEGF) was also found to have IRES element (Stein et al. (1998) *Mol Cell Biol* 18:3112-3119; Huez et al. (1998) *Mol Cell Biol* 18:6178-6190).

An IRES sequence may be tested and compared to a 2A sequence as shown in Example 1. In one exemplary protocol a test vector or plasmid is generated with one transgene, such as PF-4 or VEGF-TRAP, placed under translational control of an IRES, 2A or 2A-like sequence to be tested. A cell is transfected with the vector or plasmid containing the IRES- or 2A-reporter gene sequences and an assay is performed to detect the presence of the transgene. In one illustrative example, the test plasmid comprises co-transcribed PF-4 and VEGF-TRAP coding sequences transcriptionally driven by a CMV promoter wherein the PF4 or VEGF-TRAP coding sequence is translationally driven by the IRES, 2A or 2A-like sequence to be tested. Host cells are transiently transfected with the test vector or plasmid by means known to those of skill in the art and assayed for the expression of the transgene.

IRES may be prepared using standard recombinant and synthetic methods known in the art. For cloning convenience, restriction sites may be engineered into the ends of the IRES fragments to be used.

To express two or more proteins from a single viral or non-viral vector, an internal ribosome entry site (IRES) sequence is commonly used to drive expression of the second, third, fourth gene, etc. Although the use of an IRES is considered to be the state of the art by many, when two genes are linked via an IRES, the expression level of the second gene is often significantly reduced (Furler et al., Gene Therapy 8:864-873 (2001)). In fact, the use of an IRES to control transcription of two or more genes operably linked to the same promoter can result in lower level expression of the second, third, etc. gene relative to the gene adjacent the pro- The linking of proteins in the form of polyproteins is a strategy adopted in the replication of many viruses including picornaviridae. Upon translation, virus-encoded self-processing peptides mediate rapid intramolecular (cis) cleavage of the polyprotein to yield discrete mature protein products. The present invention provides advantages over the use of an IRES in that a vector for recombinant protein or polypeptide expression comprising a self-processing peptide (exemplified herein by 2A peptides) is provided which facilitates expression of two or more protein or polypeptide coding sequences using a single promoter, wherein the two or more proteins or polypeptides are expressed in a substantially equimolar ratio.

Self-Processing Cleavage Sites or Sequences

A "self-processing cleavage site" or "self-processing cleavage sequence" as defined above refers to a DNA or amino acid sequence, wherein upon translation, rapid intramolecular (cis) cleavage of a polypeptide comprising the self-processing cleavage site occurs to result in expression of discrete mature protein or polypeptide products. Such a "self-processing cleavage site", may also be referred to as a post-translational or co-translational processing cleavage site, exemplified herein by a 2A site, sequence or domain. It has been reported that a 2A site, sequence or domain demonstrates a translational effect by modifying the activity of the ribosome to promote hydrolysis of an ester linkage, thereby releasing the polypeptide from the translational complex in a manner that allows the synthesis of a discrete downstream translation product to proceed (Donnelly, 2001). Alternatively, a 2A site, sequence or domain demonstrates "auto-proteolysis" or "cleavage" by cleaving its own C-terminus in cis to produce primary cleavage products (Furler; Palmenberg, Ann. Rev. Microbiol. 44:603-623 (1990)).

Although the mechanism is not part of the invention, the activity of a 2A-like sequence may involve ribosomal skipping between codons which prevents formation of peptide bonds (de Felipe et al., Human Gene Therapy 11:1921-1931 (2000); Donnelly et al., J. Gen. Virol. 82:1013-1025 (2001)), although it has been considered that the domain acts more like an autolytic enzyme (Ryan et al., Virol. 173:35-45 (1989).

Studies in which the Foot and Mouth Disease Virus (FMDV) 2A coding region was cloned into expression vectors and transfected into target cells showed FMDV 2A cleavage of artificial reporter polyproteins in wheat-germ lysate and transgenic tobacco plants (Halpin et al., U.S. Pat. No. 5,846, 767; 1998 and Halpin et al., The Plant Journal 17:453-459, 1999); Hs 683 human glioma cell line (de Felipe et al., Gene Therapy 6:198-208, 1999); hereinafter referred to as "de Felipe II"); rabbit reticulocyte lysate and human HTK-143 cells (Ryan et al., EMBO J. 13:928-933 (1994)); and insect cells (Roosien et al., J. Gen. Virol. 71:1703-1711, 1990). The FMDV 2A-mediated cleavage of a heterologous polyprotein has been shown for IL-12 (p40/p35 heterodimer; Chaplin et al., J. Interferon Cytokine Res. 19:235-241, 1999). The reference demonstrates that in transfected COS-7 cells, FMDV 2A mediated the cleavage of a p40-2A-p35 polyprotein into biologically functional subunits p40 and p35 having activities associated with IL-12.

The FMDV 2A sequence has been incorporated into retroviral vectors, alone or combined with different IRES sequences to construct bicistronic, tricistronic and tetracistronic vectors. The efficiency of 2A-mediated gene expression in animals was demonstrated by Furler (2001) using recombinant adeno-associated viral (AAV) vectors encoding α-synuclein and EGFP or Cu/Zn superoxide dismutase (SOD-1) and EGFP linked via the FMDV 2A sequence. EGFP and α-synuclein were expressed at substantially higher levels from vectors which included a 2A sequence relative to corresponding IRES-based vectors, while SOD-1 was expressed at comparable or slightly higher levels. Fuder also demonstrated that the 2A sequence results in bicistronic gene expression in vivo after injection of 2A-containing AAV vectors into rat substantia nigra.

For the present invention, the DNA sequence encoding a self-processing cleavage site is exemplified by viral sequences derived from a picornavirus, including but not limited to an entero-, rhino-, cardio-, aphtho- or Foot-and-Mouth Disease Virus (FMDV). In a preferred embodiment, the self-processing cleavage site coding sequence is derived from a FMDV. Self-processing cleavage sites include but are not limited to 2A and 2A-like sites, sequences or domains (Donnelly et al., J. Gen. Virol. 82:1027-1041 (2001).

Positional subcloning of a 2A sequence between two or more heterologous DNA sequences for the inventive vector construct allows the delivery and expression of two or more open reading frames by operable linkage to a single promoter. Preferably, self processing cleavage sites such as FMDV 2A sequences provide a unique means to express and deliver from a single viral vector, two or more proteins, polypeptides or peptides which can be individual parts of, for example, Factor VIII or another heterodimeric protein, an antibody, or a heterodimeric receptor.

FMDV 2A is a polyprotein region which functions in the FMDV genome to direct a single cleavage at its own C-terminus, thus functioning in cis. The FMDV 2A domain is typically reported to be about nineteen amino acids in length ((LLNFDLLKLAGDVESNPGP (SEQ ID NO: 1); TLNFDLLKLAGDVESNPGP (SEQ ID NO: 2); Ryan et al., J. Gen. Virol. 72:2727-2732 (1991)), however oligopeptides of as few as fourteen amino acid residues ((LLKLAGDVESNPGP (SEQ ID NO: 3)) have also been shown to mediate cleavage at the 2A C-terminus in a fashion similar to its role in the native FMDV polyprotein processing.

Variations of the 2A sequence have been studied for their ability to mediate efficient processing of polyproteins (Donnelly MLL et al. 2001). Homologues and variant 2A sequences are included within the scope of the invention and include but are not limited to the sequences presented in Table 2, below:

TABLE 2

Table of Exemplary 2A Sequences

| | |
|---|---|
| LLNFDLLKLAGDVESNPGP | (SEQ ID NO: 1) |
| TLNFDLLKLAGDVESNPGP; | (SEQ ID NO: 2) |
| LLKLAGDVESNPGP | (SEQ ID NO: 3) |
| NFDLLKLAGDVESNPGP | (SEQ ID NO: 4) |
| QLLNFDLLKLAGDVESNPGP | (SEQ ID NO: 5) |
| APVKQTLNFDLLKLAGDVESNPGP. | (SEQ ID NO: 6) |
| VTELLYRMKRAETYCPRPLLAIHPTEARHKQKIVAPVKQTLNFDLLKLA GDVESNPGP | (SEQ ID NO: 7) |
| LLAIHPTEARHKQKIVAPVKQTLNFDLLKLAGDVESNPGP | (SEQ ID NO: 8) |
| EARHKQKIVAPVKQTLNFDLLKLAGDVESNPGP | (SEQ ID NO: 9) |

Distinct advantages of self-processing cleavage sequences, such as a 2A sequence or a variant thereof are their use in generating vectors expressing self-processing polyproteins. This invention includes any vector (plasmid or viral based) which comprises the coding sequence for two or more proteins or polypeptides linked via self-processing cleavage sites such that the individual proteins or polypeptides are expressed in equimolar or close to equimolar amounts following the cleavage of the polyprotein due to the presence of the self-processing cleavage site. These proteins may be heterologous to the vector itself, to each other or to the self-processing cleavage site, e.g., FMDV. Thus the self-processing cleavage sites for use in practicing the invention do not discriminate between heterologous proteins or polypeptides and coding sequences derived from the same source as the self-processing cleavage site, in the ability to function or mediate cleavage.

The small size of the 2A coding sequence further enables its use in vectors with a limited packing capacity for a coding sequence such as AAV. The utility of AAV vectors can be further expanded since the 2A sequence eliminates the need for dual promoters. The expression levels of individual proteins, polypeptides or peptides from a promoter driving a single open reading frame comprising more than two coding sequences are closer to equimolar as compared to expression levels achievable using IRES sequences or dual promoters. Elimination of dual promoters reduces promoter interference that may result in reduced and/or impaired levels of expression for each coding sequence.

In one preferred embodiment, the FMDV 2A sequence included in a vector according to the invention encodes amino acid residues comprising LLNFDLLKLAGDVESNPGP (SEQ ID NO:1). Alternatively, a vector according to the invention may encode amino acid residues for other 2A-like regions as discussed in Donnelly et al., J. Gen. Virol. 82:1027-1041 (2001) and including but not limited to a 2A-like domain from picornavirus, insect virus, Type C rotavirus, trypanosome repeated sequences or the bacterium, Thermatoga maritima.

The invention contemplates the use of nucleic acid sequence variants that encode a self-processing cleavage site, such as a 2A or 2A-like polypeptide, and nucleic acid coding sequences that have a different codon for one or more of the amino acids relative to that of the parent (native) nucleotide. Such variants are specifically contemplated and encompassed by the present invention. Sequence variants of self-processing cleavage peptides and polypeptides are included within the scope of the invention as well.

As used herein, the term "sequence identity" means nucleic acid or amino acid sequence identity between two or more aligned sequences, when aligned using a sequence alignment program. The terms "% homology" and "% identity" are used interchangeably herein and refer to the level of nucleic acid or amino acid sequence identity between two or more aligned sequences, when aligned using a sequence alignment program. For example, 80% homology means the same thing as 80% sequence identity determined by a defined algorithm under defined conditions.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the BLAST algorithm, Altschul et al., J. Mol. Biol. 215: 403-410 (1990), with software that is publicly available through the National Center for Biotechnology Information (http://www.ncbi.nlm.nih.gov/), or by visual inspection (see generally, Ausubel et al., infra). For purposes of the present invention, optimal alignment of sequences for comparison is most preferably conducted by the local homology algorithm of Smith & Waterman, Adv. Appl. Math. 2: 482 (1981). See, also, Altschul, S. F. et al., 1990 and Altschul, S. F. et al., 1997.

The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the sequence comparison algorithms described herein, e.g. the Smith-Waterman algorithm, or by visual inspection.

In accordance with the present invention, also encompassed are sequence variants which encode self-processing cleavage polypeptides and polypeptides themselves that have 80, 85, 88, 89, 90, 91, 92, 93, 94, 95, 96, 97, 98, 99% or more sequence identity to the native sequence.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993. An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1× SSC and 0.5% SDS at 42° C. 2A sequence variants that encode a polypeptide with the same biological activity as the 2A polypeptides described herein and hybridize under moderate to high stringency hybridization conditions are considered to be within the scope of the present invention.

As a result of the degeneracy of the genetic code, a number of coding sequences can be provided which encode the same protein, polypeptide or peptide, such as 2A or a 2A-like peptide. For example, the triplet CGT encodes the amino acid arginine. Arginine is alternatively encoded by CGA, CGC, CGG, AGA, and AGG. Therefore it is appreciated that such substitutions in the coding region fall within the sequence variants that are covered by the present invention.

It is further appreciated that such sequence variants may or may not hybridize to the parent sequence under conditions of high stringency. This would be possible, for example, when the sequence variant includes a different codon for each of the amino acids encoded by the parent nucleotide. Such variants are, nonetheless, specifically contemplated and encompassed by the present invention.

Removal of Self-Processing Peptide Sequences.

One concern associated with the use of self-processing peptides, such as a 2A or 2A-like sequence is that the C terminus of the expressed polypeptide contains amino acids derived from the self-processing peptide, i.e. 2A-derived amino acid residues. These amino acid residues are "foreign" to the host and may elicit an immune response when the recombinant protein is expressed in vivo (i.e., expressed from a viral or non-viral vector in the context of gene therapy or administered as an in vitro-produced recombinant protein or polypeptide) or delivered in vivo following in vitro or ex vivo expression. In addition, if not removed, self-processing peptide-derived amino acid residues may interfere with protein secretion in producer cells and/or alter protein conformation, resulting in a less than optimal expression level and/or reduced biological activity of the recombinant protein.

The invention includes expression constructs, engineered such that an additional proteolytic cleavage site is provided between a first protein or polypeptide coding sequence (the first or 5' ORF) and the self processing cleavage site as a means for removal of self processing cleavage site derived amino acid residues that are present in the expressed protein product.

Examples of additional proteolytic cleavage sites are furin cleavage sites with the consensus sequence RXK(R)R (SEQ ID NO: 10), which can be cleaved by endogenous subtilisin-like proteases, such as furin and other serine proteases. As shown in Example 6, the inventors have demonstrated that self processing 2A amino acid residues at the C terminus of a first expressed protein can be efficiently removed by introducing a furin cleavage site RAKR (SEQ ID NO: 38) between the first polypeptide and a self processing 2A sequence. In addition, use of a plasmid containing a 2A sequence and a furin cleavage site adjacent to the 2A sequence was shown to result in a higher level of protein expression than a plasmid containing the 2A sequence alone. This improvement provides a further advantage in that when 2A amino acid residues are removed from the C-terminus of the protein, longer 2A- or 2A like sequences or other self-processing sequences can be used.

It is often advantageous to produce therapeutic proteins, polypeptides, fragments or analogues thereof with fully human characteristics. These reagents avoid the undesired immune responses induced by proteins, polypeptides, fragments or analogues thereof originating from different species. To address possible host immune responses to amino acid residues derived from self-processing peptides, the coding sequence for a proteolytic cleavage site may be inserted (using standard methodology known in the art) between the coding sequence for a first protein and the coding sequence for a self-processing peptide so as to remove the self-processing peptide sequence from the expressed protein or polypeptide. This finds particular utility in therapeutic and diagnostic proteins and polypeptides for use in vivo.

Any additional proteolytic cleavage site known in the art that can be expressed using recombinant DNA technology may be employed in practicing the invention. Exemplary additional proteolytic cleavage sites which can be inserted between a polypeptide or protein coding sequence and a self processing cleavage sequence include, but are not limited to a:

a). Furin consensus sequence or site: RXK(R)R (SEQ ID. NO:10);
b). Factor Xa cleavage sequence or site: IE(D)GR (SEQ ID. NO:11);
c). Signal peptidase I cleavage sequence or site: e.g., LAGFATVAQA (SEQ ID. NO:12); and
d). Thrombin cleavage sequence or site: LVPRGS (SEQ ID. NO:13).

Protein Coding Sequences

As used herein, a "first protein coding sequence" refers to a heterologous nucleic acid sequence encoding a polypeptide or protein molecule or domain or chain thereof including, but not limited to a chain of an antibody or immunoglobulin molecule or fragment thereof, a cytokine or fragment thereof, a growth factor or fragment thereof, a chain of a Factor VIII molecule, a soluble or membrane-associated receptor or fragment thereof, a viral protein or fragment thereof, an immunogenic protein or fragment thereof, a transcriptional regulator or fragment thereof, a proapoptotic molecule or fragment thereof, a tumor suppressor or fragment thereof, an angiogenesis inhibitor or fragment thereof, etc.

As used herein, a "second protein coding sequence" refers to a heterologous nucleic acid sequence encoding: a polypeptide or protein molecule or domain or chain thereof including, but not limited to a chain of an antibody or immunoglobulin or fragment thereof, a cytokine or fragment thereof, a growth factor or fragment thereof, a chain of a Factor VIII molecule, a soluble or membrane-associated receptor or fragment thereof, a viral protein or fragment thereof, an immunogenic protein or fragment thereof, a transcriptional regulator or fragment thereof, a proapoptotic molecule or fragment thereof, a tumor suppressor or fragment thereof, an angiogenesis inhibitor or fragment thereof, etc.

The vector constructs of the invention may comprise two or more transgenes or heterologous coding sequences, e.g., a first protein coding sequence, a second protein coding sequence, a third protein coding sequence, etc. Numerous transgenes may be employed in the practice of the present invention and include, but are not limited to, nucleotide sequences encoding one or more of the proteins indicated below or a fragment thereof:

1. A sequence encoding HIF-1α and HIFβ (HIF), p35 and p40 (IL-12), chain A and chain B of insulin, integrins such as, but not limited to alpha V beta 3 or alpha V beta 5, antibody heavy and light chains and the heavy and light chain of Factor VIII.

2. A sequence encoding a soluble receptor, include but are not limited to, the TNF p55 and p75 receptor, the IL-2 receptor, the FGF receptors, the VEGF receptors, TIE2, the IL-6 receptor and the IL-1 receptor;

3. A sequence encoding a cytokine including, but not limited to, any known or later discovered cytokine, for example, IL-1, IL-2, IL-3, IL-4, IL-5, IL-6, IL-7, IL-8, IL-9, IL-10, IL-11, IL-12, IL-13, IL-18, IL-24, INF-α, INF-β, INF-γ, GM-CSF, G-CSF and erythropoietin.

4. A sequence encoding a growth factor including, but not limited to, VEGF, FGF, Angiopoietin-1 and 2, PDGF, EGF, IGF, NGF, IDF, HGF, TGF-α, TGF-beta.

5. A sequence encoding a pro-apoptotic factor including, but not limited to, Bad, Bak, Bax, Bcl2, Bcl-Xs, Bik, Caspases, FasL, and TRAIL.

6. A sequence encoding a tumor suppressor protein or cell cycle regulator including, but not limited to, p53, p16, p19, −21, p27, PTEN, RB1.

7. A sequence encoding an angiogenesis regulator including, but not limited to, angiostatin, endostatin, TIMPs, antithrombin, platelet factor 4 (PF4), soluble forms of VEGFR1 (domains 1-7) and VEGFR2 (domains 1-7) fused to an Fc segment of IgG1, VEGF-TRAP, PEDF, PEX, troponin I, thrombospondin, tumstatin, 16 Kd Prolactin.

Cloned sequences and full length nucleotides encoding any of the above-referenced biologically active molecules may be obtained by well known methods in the art (Sambrook et al., 1989). In general, the nucleic acid coding sequences are known and may be obtained from public databases and/or scientific publications.

Homologues and variants of heterologous protein and polypeptide coding sequences are included within the scope of the invention based on "sequence identity" or "% homology" to known nucleic acid sequences which are available in public databases and/or selective hybridization under stringent conditions to such known nucleic acid sequences, as described above for self processing cleavage sequences. Homologues and variants of heterologous protein and polypeptide amino acid sequences and nucleic acid sequences that encode them are further included within the scope of the invention. Such sequences may be identified based on "sequence identity" to known sequences using publicly available databases and sequence alignment programs, as described above for self processing cleavage sequences.

Protein Expression

High level expression of therapeutic proteins has been successfully demonstrated in the milk of transgenic goats. Taking monoclonal antibodies as an example, it has been shown that antigen binding levels are equivalent to that of monoclonal antibodies produced using conventional cell culture technology. This method is based on development of human therapeutic proteins in the milk of transgenic animals, which carry genetic information allowing them to express human therapeutic proteins in their milk. Once they are produced, these recombinant proteins can be efficiently purified from milk using standard technology. See e.g., Pollock, D. P. et al., Journal of Immunological Methods. 231: 147-157, 1999 and Young, M. W. et al., Res Immunol. July-August; 149(6): 609-610, 1998. Animal milk, egg white, blood, urine, seminal plasma and silk worm cocoons from transgenic animals have demonstrated potential as sources for production of recombinant proteins at an industrial scale (Houdebine L M, Curr Opin Biotechnology, 13: 625-629, 2002; Little M et al., Immunol Today, 21(8):364-70, 2000; and Gura T, Nature, 417:584-586, 2002). The invention contemplates use of transgenic animal expression systems for expression of a recombinant protein or polypeptide using the self-processing cleavage site-encoding vectors of the invention.

Production of recombinant proteins in plants has also been successfully demonstrated including, but not limited to rice transformed by *Agrobacterium* infection, recombinant human GM-CSF expression in the seeds of transgenic tobacco plants and expression of single-chain antibodies in plants. See, e.g., Streatfield S J, Howard J A, Int J. Parasitol. 33(5-6):479-93, 2003; Schillberg S. et al., Cell Mol Life Sci. 60(3):433-45, 2003; Pogue G P et al., Annu Rev Phytopathol. 40:45-74, 2002; and McCormick AA et al., J Immunological Methods, 278(1-2):95-104, 2003. The invention contemplates use of transgenic plant expression systems for expression of a recombinant protein or polypeptide using the self-processing cleavage site-encoding vectors of the invention.

Baculovirus vector expression systems in conjunction with insect cells are also gaining ground as a viable platform for recombinant protein production. Baculovirus vector expression systems have been reported to provide advantages relative to mammalian cell culture expression systems such as ease of culture and higher expression levels. See, e.g., Ghosh S. et al., Mol Ther. 2002 July; 6(1):5-11, 2002 and Ikonomou L et al., Appl Microbiol Biotechnol. 62(1):1-20, 2003. The invention further contemplates use of Baculovirus vector expression systems for expression of a recombinant protein or polypeptide using the self-processing cleavage site-encoding vectors of the invention.

Yeast-based systems may also be employed for expression of a recombinant protein or polypeptide using the self-processing cleavage site-encoding vectors of the invention. See, e.g., Stuart, WD (1997): "Heterologous dimeric proteins produced in heterokaryons"; U.S. Pat. No. 5,643,745.

It will be understood that the vectors of the invention which comprise the coding sequence for a self-processing peptide alone or in combination with an additional coding sequence for a proteolytic cleavage site find utility in the expression of recombinant proteins and polypeptides in any protein expression system, a number of which are known in the art and examples of which are described herein. One of skill in the art may easily adapt the vectors of the invention for use in any protein expression system.

Following expression, recombinant proteins are recovered from the culture using standard techniques known in the art. The production and recovery of recombinant proteins themselves can be achieved in various ways numerous examples of which are known in the art. For example, the production of a recombinant protein, polypeptide, an analogue or fragment thereof, can be undertaken by culturing the modified recombinant host cell under culture conditions appropriate that host cell resulting in expression of the coding sequence(s). In order to monitor the success of expression, recombinant protein or polypeptide levels are monitored using standard techniques such as ELISA, RIA, Western blot and the like.

Purified forms of the recombinant proteins can, of course, be readily prepared by standard purification techniques known in the art, e.g., affinity chromatography. Recombinant proteins can also be purified using conventional chromatography, such as an ion exchange or size exclusion column, in conjunction with other technologies, such as size-limited membrane filtration. The expression systems are preferably designed to include signal peptides so that the resulting recombinant proteins are secreted into the medium, however, intracellular production is also possible.

The operability of the present invention has been further demonstrated by expression of platelet factor 4 (PF4) and VEGF-TRAP using the self processing cleavage sequence-containing vectors of the present invention (Example 1). The advantages associated with use of self-processing cleavage sequences are enhanced by inclusion of an additional proteolytic cleavage site between the coding sequence for a first protein or polypeptide and the self-processing cleavage sequence in the vectors of the invention, resulting in removal of amino acid residues associated with the self-processing cleavage sequence. Efficient removal of 2A residues by incorporation of a furin cleavage site in the vectors of the invention is demonstrated in Examples 6 and 7.

A. Platelet Factor 4 (PF4) and VEGF-TRAP

Platelet factor 4 (PF-4) is a member of the CXC family of chemokines and has been shown to be a potent in vitro inhibitor of endothelial cell proliferation and an in vivo inhibitor of angiogenesis (Maione, T E et al. Science 237:77-79, 1990). Furthermore, recombinant PF-4 has been shown to inhibit the growth of B16F10 melanoma and HCT colon carcinoma cells (Sharpe, R J et al. J. Natl. Cancer Inst. 82:848-853, 1990, Kolber et al. J. Natl. Cancer Inst. 87:304-309, 1995). Adenoviral or retroviral delivery of a secreted form of PF-4 (sPF-4) was further shown to inhibit the growth of rat RT2 and human U87MG glioma cells through an angiogenesis-dependent mechanism (Tanaka et al., Nat. Med. 3:437-442, 1997). PF-4 appears to block angiogenesis by interfering with the binding of FGF-2 and VEGF binding to their receptors (Perollet, C. Blood 91:3289-3299, 1998, Gengrinovitch et al, J. Biol. Chem. 270:15059-15065, 1995).

VEGF-Trap consists of the signal sequence and domain 2 of VEGFR1 attached to domain 3 of VEGFR2 and a human IgG Fc region (Holash et al. Proc. Natl. Acad. Sci. USA. 99(17):11393-8, 2002;). Each of the domains was PCR amplified separately using the oligonucleotides shown below, and the resulting products were fused by PCR SOEing to generate the final nucleotide sequence. The nucleotide sequences for VEGFR1 and VEGF-R2 were obtained from the plasmids pBLAST-hFLT1 (Invivogen) and pBLAST-hFLK1 (Invivogen).

B. Factor VIII

Hemophilia A is an X-linked recessive bleeding disorder characterized by a deficiency or functional defect in the coagulation Factor VIII. There are approximately 20,000 Hemophilia A patients in the United States, and the cost of treatment for severely affected individuals approaches 100,000 per year. Without Factor VIII, patients can experience life-threatening blood loss from minor scrapes and cuts. The severity of symptoms associated with hemophilia is related to the amount of the clotting factor in the blood. If the level of circulating Factor VIII in hemophilia patients is increased to five percent of the normal level of Factor VIII, symptoms are mild, with rare bleeding except after injuries or surgery. The most important challenges facing the hemophilia patient are the availability, cost, and safety of products used for treatment. Plasma derived Factor VIII concentrates were extensively used in the 1970s and 1980s. Unfortunately, these concentrates carried a significant risk of viral contamination. Factor VIII is now available in several different recombinant forms, however therapy is limited by the availability, in vivo half-life, and the high cost of treatment. The recombinant Factor VIII products include a natural full-length recombinant Factor VIII form, and a B-domain deleted recombinant Factor VIII form.

In plasma, Factor VIII exists as a metal ion heterodimer of a variably sized 90-200 kDa heavy chain and 80 kDa light chain. The mature Factor VIII protein contains 2332 amino acids arranged in six domains, namely A1 (residues 1-336), A2 (372-710), B (741-1648), A3 (1896-2019), C1 (2020-2172), C2 (2173-2332). The heavy chain encodes the A1, A2, and B domains, whereas the light chain encodes the A3, C1, and C2 domains. The Factor VIII protein is highly glycosylated and contains 25 consensus sites for N-linked glycosylation, 19 of which are located in the B-domain. The B-domain is proteolytically released upon activation by thrombin and is not required for Factor VIII procoagulant activity in vitro or in vivo (Lenting, P. J., et al (1998) Blood 92 11, 3983-3996). A number of B-domain deleted forms of Factor VIII have been generated. Common Factor VIII constructs include those where the B-domain is completely removed or replaced with 1-4 Arg residues (Lind, P., et al. Eur J Biochem 232 1, 19-27, 1995). Removal of the B-domain has no adverse effect on protein activity, and results in an approximately 20-fold increase in level of Factor VIII (Pittman et al., Blood 81:2925-2935, 1993).

Gene therapy was thought to offer the promise of a new method of treating Hemophilia A. However, although numerous reports of Factor VIII expression using gene delivery technology may be found in the scientific literature, production of therapeutic levels of the protein remains a challenge (Vandendriessche et al., J. Thromb. Haemost. 1:1550-1558, 2003).

Figure 3:
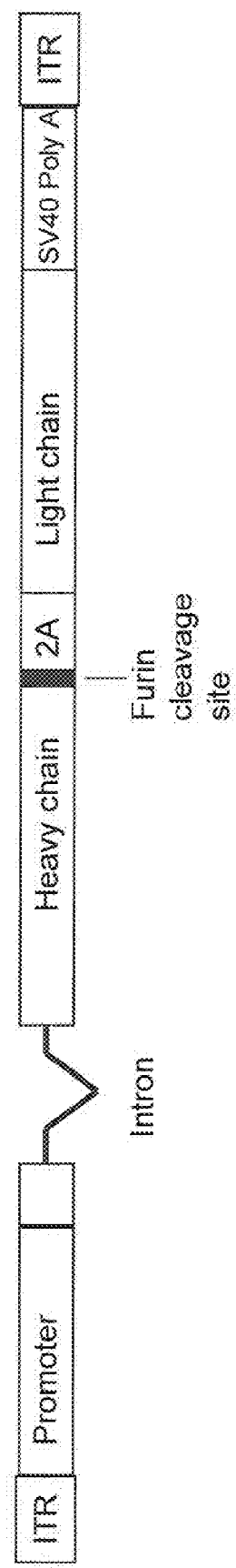
FIG. 3 depicts an expression cassette for expression of two polypeptides (Factor VIII heavy and light chains) as described in Example 2.

The present invention provides improved vectors and methods for the expression of Factor VIII protein or a functional variant thereof. The method comprises the stable introduction of a nucleic acid construct encoding the Factor VIII polypeptide or a functional variant thereof and a self-processing cleavage site into a cell in vivo, in vitro or ex vivo. The nucleic acid sequence encoding Factor VIII may contain genomic or complementary DNA. There are many applications for this method, including the manufacturing of recombinant Factor VIII used in the prophylactic and acute treatment of Hemophilia A. Other applications include the in vivo and ex vivo delivery of Factor VIII to patients, e.g., using AAV or lentiviral vectors. An example of an AAV vector containing the Factor VIII gene is shown in FIG. 3.

It is not intended that the present invention be limited to any specific Factor VIII sequence or gene delivery mechanism. Many natural and recombinant forms of Factor VIII have been identified and characterized. Therefore, included within the scope of the invention are any known, or later discovered, DNA sequences coding for biologically active Factor VIII that can be expressed using the vectors and methods of the present invention. Examples of naturally occurring and recombinant forms of Factor VIII can be found in the patent and scientific literature including, but not limited to High K A, Semin Thromb Hemost. 2003 February; 29(1):107-20; Thompson A R. Semin Thromb Hemost. 2003 February; 29(1):11-22; Sandberg H et al., Semin Hematol. 2001 April; 38(2 Suppl 4):4-12; Brinkhous K et al., Semin Thromb Hemost. 2002 June; 28(3):269-72; Osterberg T et al., Semin Hematol. 2001 April; 38(2 Suppl 4):40-3; Kjalke M et al., Eur J. Biochem. 1995 December 15; 234(3):773-9; Lind P et al., Eur J Biochem. 1995 August 15; 232(1):19-27; Sanberg et al., XXth Int. Congress of the World Fed. Of Hemophilia (1992); U.S. Pat. Nos. 6,649,375; 6,649,375; 6,642,028; 6,599,724; 6,518,482; 6,517,830; 6,458,563; 6,376,463; 6,358,703; 6,358,236; 6,320,029; 6,271,025; 6,251,632; 6,221,349; 6,200,560; 6,180,371; PCT Publication Nos. WO 03/100053; WO 03/087161; WO 03/080108; WO 03/047507; WO 03/031598; WO 02/072023; WO 02/24723; WO 01/68109; WO 01/45510; WO 01/27303; WO 01/03726; WO 00/71141; WO 00/23116; WO 99/61642; WO 99/61595; WO 99/46299; WO 99/46274; and WO 97/49725.

Homologues and variants of Factor VIII nucleic acid and amino acid sequences are included within the scope of the invention based on "sequence identity" or "% homology" to known nucleic acid sequences which are available in public databases and/or selective hybridization under stringent conditions in the case of nucleic acid sequences, as described above for self processing cleavage sequences.

It will be understood that the vectors of the invention which comprise the coding sequence for a self-processing peptide alone or in combination with an additional proteolytic cleavage site find utility in the expression of recombinant Factor VIII in any protein expression system, a number of which are known in the art and examples of which are described herein.

Recombinant Factor VIII is recovered from the culture medium if expressed in vitro, or from plasma or other body fluids if expressed in vivo using standard techniques routinely used by those of skill in the art. Methods such as immunoassay (e.g., ELISA) and coagulation assays are typically employed in evaluating the production of Factor VIII and the biological activity thereof, however, it is not intended that the present invention be limited to any particular method of evaluation.

C. Immunoglobulins and Fragments Thereof

Antibodies are immunoglobulin proteins that are heterodimers of a heavy and light chain and have proven difficult to express in a full length form from a single vector in mammalian culture expression systems. Three methods are currently used for production of vertebrate antibodies, in vivo immunization of animals to produce "polyclonal" antibodies, in vitro cell culture of B-cell hybridomas to produce monoclonal antibodies (Kohler, et al., Eur. J. Immunol., 6: 511, 1976; Antibodies: A Laboratory Manual, Cold Spring Harbor Laboratory, 1988) and recombinant DNA technology (described for example in Cabilly et al., U.S. Pat. No. 6,331,415).

The basic molecular structure of immunoglobulin polypeptides is known to include two identical light chains with a molecular weight of approximately 23,000 daltons, and two identical heavy chains with a molecular weight 53,000-70,000, where the four chains are joined by disulfide bonds in a "Y" configuration. The amino acid sequence runs from the N-terminal end at the top of the Y to the C-terminal end at the bottom of each chain. At the N-terminal end is a variable region (of approximately 100 amino acids in length) which provides for the specificity of antigen binding.

The present invention provides improved methods for production of immunoglobulins of all types, including, but not limited to full length antibodies and antibody fragments having a native sequence (i.e. that sequence produced in response to stimulation by an antigen), single chain antibodies which combine the antigen binding variable region of both the heavy and light chains in a single stably-folded polypeptide chain; univalent antibodies (which comprise a heavy chain/light chain dimer bound to the Fc region of a second heavy chain); "Fab fragments" which include the full "Y" region of the immunoglobulin molecule, i.e., the branches of the "Y", either the light chain or heavy chain alone, or portions, thereof (i.e., aggregates of one heavy and one light chain, commonly known as Fab'); "hybrid immunoglobulins" which have specificity for two or more different antigens (e.g., quadromas or bispecific antibodies as described for example in U.S. Pat. No. 6,623,940); "composite immunoglobulins" wherein the heavy and light chains mimic those from different species or specificities; and "chimeric antibodies" wherein portions of each of the amino acid sequences of the heavy and light chain are derived from more than one species (i.e., the variable region is derived from one source such as a murine antibody, while the constant region is derived from another, such as a human antibody).

The compositions and methods of the invention find utility in production of immunoglobulins or fragments thereof wherein the heavy or light chain is "mammalian", "chimeric" or modified in a manner to enhance its efficacy. Modified antibodies include both amino acid and nucleic acid sequence variants which retain the same biological activity of the unmodified form and those which are modified such that the activity is altered, i.e., changes in the constant region that improve complement fixation, interaction with membranes, and other effector functions, or changes in the variable region that improve antigen binding characteristics. The compositions and methods of the invention further include catalytic immunoglobulins or fragments thereof.

A "variant" immunoglobulin-encoding polynucleotide sequence may encode a "variant" immunoglobulin amino acid sequence which is altered by one or more amino acids from the reference polypeptide sequence. The variant polynucleotide sequence may encode a variant amino acid sequence which contains "conservative" substitutions, wherein the substituted amino acid has structural or chemical properties similar to the amino acid which it replaces. In addition, or alternatively, the variant polynucleotide sequence may encode a variant amino acid sequence which contains "non-conservative" substitutions, wherein the substituted amino acid has dissimilar structural or chemical properties to the amino acid which it replaces. Variant immunoglobulin-encoding polynucleotides may also encode variant amino acid sequences which contain amino acid insertions or deletions, or both. Furthermore, a variant "immunoglobulin-encoding polynucleotide" may encode the same polypeptide as the reference polynucleotide sequence but, due to the degeneracy of the genetic code, has a polynucleotide sequence altered by one or more bases from the reference polynucleotide sequence.

The term "fragment," when referring to a recombinant immunoglobulin of the invention means a polypeptide which has an amino acid sequence which is the same as part of but not all of the amino acid sequence of the corresponding full length immunoglobulin protein, which either retains essentially the same biological function or activity as the corresponding full length protein, or retains at least one of the functions or activities of the corresponding full length protein. The fragment preferably includes at least 20-100 contiguous amino acid residues of the full length immunoglobulin.

The potential of antibodies as therapeutic modalities is currently limited by the production capacity and excessive cost of the current technology. An improved viral or non-viral single expression vector for immunoglobulin production would permit the expression and delivery of two or more coding sequences, i.e., immunoglobulins with bi- or multiple-specificities from a single vector. The present invention addresses these limitations and is applicable to any immunoglobulin (i.e. an antibody) or fragment thereof as further detailed herein, including engineered antibodies such as single chain antibodies, full-length antibodies or antibody fragments.

Antibody Production

In one example of the present invention, the coding sequence for a first or second chain of a protein or polypeptide is the coding sequence for the heavy chain or a fragment thereof for any immunoglobulin, e.g., IgG, IgM, IgD, IgE or IgA. Alternatively, the coding sequence for a first or second chain of a protein or polypeptide is the coding sequence for the light chain or a fragment thereof for an IgG, IgM, IgD, IgE or IgA. Genes for whole antibody molecules as well as modified or derived forms thereof, such as fragments, e.g., Fab, single chain Fv(scFv) and F(ab')$_2$ are include within the scope of the invention. The antibodies and fragments can be animal-derived, human-mouse chimeric, humanized, DeImmunized™ or fully human. The antibodies can be bispecific and include but are not limited to diabodies, quadroma, mini-antibodies, ScBs antibodies and knobs-into-holes antibodies.

In practicing the invention, the production of an antibody, or variant (analogue) or fragment thereof using recombinant DNA technology can be achieved by culturing a modified recombinant host cell under culture conditions appropriate for the growth of that host cell resulting in expression of the coding sequences. In order to monitor the success of expression, antibody levels with respect to the antigen may be monitored using standard techniques such as ELISA, RIA, Western blot and the like. The antibodies are recovered from the culture supernatant using standard techniques known in the art. Purified forms of these antibodies can, of course, be readily prepared by standard purification techniques, e.g., affinity chromatography via protein A, protein G or protein L columns, or based on binding to the particular antigen, or the particular epitope of the antigen for which specificity is desired. Antibodies can also be purified with conventional chromatography, such as an ion exchange or size exclusion column, in conjunction with other technologies, such as ammonia sulfate precipitation and size-limited membrane filtration. Preferred expression systems are designed to include signal peptides so that the resulting antibodies are secreted into the culture medium or supernatant, allowing for ease of purification, however, intracellular production is also possible.

The production and selection of antigen-specific fully human monoclonal antibodies from mice engineered with human Ig loci, has previously been described (Jakobovits A. et al., Advanced Drug Delivery Reviews Vol. 31, pp: 33-42 (1998); Mendez M, et al., Nature Genetics Vol. 15, pp: 146-156 (1997); Jakobovits A. et al., Current Opinion in Biotechnology Vol. 6, No. 5, pp: 561-566 (1995); Green L, et al., Nature Genetics Vol. 7, No. 1, pp: 13-21 (1994).

The production and recovery of the antibodies themselves can be achieved in various ways known in the art (Harlow et al., "Antibodies, A Laboratory Manual", Cold Spring Harbor Lab, 1988).

Vectors for Use in Practicing the Invention

The present invention contemplates the use of any of a variety of vectors for introduction of constructs comprising the coding sequence for two or more polypeptides or proteins and a self processing cleavage sequence into cells such that protein expression results. Numerous examples of expression vectors are known in the art and may be of viral or non-viral origin. Non-viral gene delivery methods which may be employed in the practice of the invention, include but are not limited to plasmids, liposomes, nucleic acid/liposome complexes, cationic lipids and the like.

Viral vectors can efficiently transduce cells and introduce their own DNA into a host cell. In generating recombinant viral vectors, non-essential genes are replaced with a gene encoding a protein or polypeptide of interest. Exemplary vectors include but are not limited to viral and non-viral vectors, such a retroviral vector (including lentiviral vectors), adenoviral (Ad) vectors including replication competent, replication deficient and gutless forms thereof, adeno-associated virus (AAV) vectors, simian virus 40 (SV-40) vectors, bovine papilloma vectors, Epstein-Barr vectors, herpes vectors, vaccinia vectors, Moloney murine leukemia vectors, Harvey murine sarcoma virus vectors, murine mammary tumor virus vectors, Rous sarcoma virus vectors and nonviral plasmids.

The vector typically comprises an origin of replication and the vector may or may not in addition comprise a "marker" or "selectable marker" function by which the vector can be identified and selected. While any selectable marker can be used, selectable markers for use in recombinant vectors are generally known in the art and the choice of the proper selectable marker will depend on the host cell. Examples of selectable marker genes which encode proteins that confer resistance to antibiotics or other toxins include, but are not limited to ampicillin, methotrexate, tetracycline, neomycin (Southern et al., J., J Mol Appl Genet. 1982; 1(4):327-41 (1982)), mycophenolic acid (Mulligan et al., Science 209:1422-7 (1980)), puromycin, zeomycin, hygromycin (Sugden et al., Mol Cell Biol. 5(2):410-3 (1985)) and G418. As will be understood by those of skill in the art, expression vectors typically include an origin of replication, a promoter operably linked to the coding sequence or sequences to be expressed, as well as ribosome binding sites, RNA splice sites, a polyadenylation site, and transcriptional terminator sequences, as appropriate to the coding sequence(s) being expressed.

Reference to a vector or other DNA sequences as "recombinant" merely acknowledges the operable linkage of DNA sequences that are not typically operably linked as isolated from or found in nature. Regulatory (expression and/or control) sequences are operatively linked to a nucleic acid coding sequence when the expression and/or control sequences regulate the transcription and, as appropriate, translation of the nucleic acid sequence. Thus expression and/or control sequences can include promoters, enhancers, transcription terminators, a start codon (i.e., ATG) 5' to the coding sequence, splicing signals for introns and stop codons.

Adenovirus gene therapy vectors are known to exhibit strong transient expression, excellent titer, and the ability to transduce dividing and non-dividing cells in vivo (Hitt et al., Adv in Virus Res 55:479-505, 2000). The recombinant Ad vectors of the instant invention comprise: (1) a packaging site enabling the vector to be incorporated into replication-defective Ad virions; (2) the coding sequence for two or more proteins or polypeptide of interest; and (3) a sequence encoding a self-processing cleavage site alone or in combination with an additional proteolytic cleavage site. Other elements necessary or helpful for incorporation into infectious virions, include the 5' and 3' Ad ITRs, the E2 genes, portions of the E4 gene and optionally the E3 gene.

Replication-defective Ad virions encapsulating the recombinant Ad vectors of the instant invention are made by standard techniques known in the art using Ad packaging cells and packaging technology. Examples of these methods may be found, for example, in U.S. Pat. No. 5,872,005. The coding sequence for two or more polypeptides or proteins of interest is commonly inserted into adenovirus in the deleted E3 region of the virus genome. Preferred adenoviral vectors for use in practicing the invention do not express one or more wild-type Ad gene products, e.g., E1a, E1b, E2, E3, and E4. Preferred embodiments are virions that are typically used together with packaging cell lines that complement the functions of E1, E2A, E4 and optionally the E3 gene regions. See, e.g. U.S. Pat. Nos. 5,872,005, 5,994,106, 6,133,028 and 6,127,175. Thus, as used herein, "adenovirus" and "adenovirus particle" refer to the virus itself or derivatives thereof and cover all serotypes and subtypes and both naturally occurring and recombinant forms, except where indicated otherwise. Such adenoviruses may be wildtype or may be modified in various ways known in the art or as disclosed herein. Such modifications include modifications to the adenovirus genome that is packaged in the particle in order to make an infectious virus. Such modifications include deletions known in the art, such as deletions in one or more of the E1a, E1b, E2a, E2b, E3, or E4 coding regions. Exemplary packaging and producer cells are derived from 293, A549 or HeLa cells. Adenovirus vectors are purified and formulated using standard techniques known in the art.

Adeno-associated virus (AAV) is a helper-dependent human parvovirus that is able to infect cells latently by chromosomal integration. Because of its ability to integrate chromosomally and its nonpathogenic nature, AAV has significant potential as a human gene therapy vector. For use in practicing the present invention rAAV virions are produced using standard methodology, known to those of skill in the art and are constructed such that they include, as operatively linked components in the direction of transcription, control sequences including transcriptional initiation and termination sequences, and the coding sequence(s) of interest. More specifically, the recombinant AAV vectors of the instant invention comprise: (1) a packaging site enabling the vector to be incorporated into replication-defective AAV virions; (2) the coding sequence for two or more proteins or polypeptide of interest; (3) a sequence encoding a self-processing cleavage site alone or in combination with an additional proteolytic cleavage site. AAV vectors for use in practicing the invention are constructed such that they also include, as operatively linked components in the direction of transcription, control sequences including transcriptional initiation and termination sequences. These components are flanked on the 5' and 3' end by functional AAV ITR sequences. By "functional AAV ITR sequences" is meant that the ITR sequences function as intended for the rescue, replication and packaging of the AAV virion.

Recombinant AAV vectors are also characterized in that they are capable of directing the expression and production of selected recombinant proteins or polypeptides of interest in target cells. Thus, the recombinant vectors comprise at least all of the sequences of AAV essential for encapsidation and the physical structures for infection of the recombinant AAV (rAAV) virions. Hence, AAV ITRs for use in the vectors of the invention need not have a wild-type nucleotide sequence (e.g., as described in Kotin, Hum. Gene Ther., 5:793-801, 1994), and may be altered by the insertion, deletion or substitution of nucleotides or the AAV ITRs may be derived from any of several AAV serotypes. Generally, an AAV vector is a vector derived from an adeno-associated virus serotype, including without limitation, AAV-1, AAV-2, AAV-3, AAV-4, AAV-5, AAV-6, AAV-7, AAV-8, etc. Preferred rAAV expression vectors have the wild type REP and CAP genes deleted in whole or part, but retain functional flanking ITR sequences.

Typically, an AAV expression vector is introduced into a producer cell, followed by introduction of an AAV helper construct, where the helper construct includes AAV coding regions capable of being expressed in the producer cell and which complement AAV helper functions absent in the AAV expression vector. As used herein, the term "AAV helper functions" refers to AAV coding regions capable of being expressed in the host cell to complement AAV viral functions missing from the rAAV vector. Typically, the AAV helper functions include the AAV rep coding region and the AAV cap coding region. The helper construct may be designed to down regulate the expression of the large Rep proteins (Rep78 and Rep68), typically by mutating the start codon following p5 from ATG to ACG, as described in U.S. Pat. No. 6,548,286.

Introduction of an AAV expression vector into a producer cell is typically followed by introduction of helper virus and/or additional vectors into the producer cell, wherein the helper virus and/or additional vectors provide accessory functions capable of supporting efficient rAAV virus production.

"Accessory functions" refer to functions that are required by AAV for replication, but are not provided by the AAV virion itself. Thus, these accessory functions and factors must be provided by the host cell, a virus (e.g., adenovirus, herpes simplex virus or vaccinia virus), or by an expression vector that is co-expressed in the same cell. Generally, the E1A and E1B, E2A, E4 and VA coding regions of adenovirus are used to supply the necessary accessory function required for AAV replication and packaging (Matsushita et al., Gene Therapy 5:938 [1998]).

The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286. Further compositions and methods for packaging are described in Wang et al. (US 2002/0168342) and include those techniques within the knowledge of those of skill in the art. Both AAV vectors and AAV helper constructs can be constructed to contain one or more optional selectable marker genes. Selectable marker genes which confer antibiotic resistance or sensitivity to an appropriate selective medium are generally known in the art.

The term "AAV virion" refers to a complete virus particle, such as a "wild-type" (wt) AAV virus particle (comprising a linear, single-stranded AAV nucleic acid genome associated with an AAV capsid protein coat). In contrast, a "recombinant AAV virion," and "rAAV virion" refers to an infectious viral particle containing a heterologous DNA sequence of interest, flanked on both sides by AAV ITRs.

In practicing the invention, host cells for producing rAAV virions include mammalian cells, insect cells, microorganisms and yeast. Host cells can also be packaging cells in which the AAV rep and cap genes are stably maintained in the host cell or producer cells in which the AAV vector genome is stably maintained and packaged. Exemplary packaging and producer cells are derived from 293, A549 or HeLa cells. AAV vectors are purified and formulated using standard techniques known in the art.

Retroviral vectors are also a common tool for gene delivery (Miller, Nature 357: 455-460, 1992). Retroviral vectors and more particularly lentiviral vectors may be used in practicing the present invention. Accordingly, the term "retrovirus" or "retroviral vector", as used herein is meant to include "lentivirus" and "lentiviral vectors" respectively. Retroviral vectors have been tested and found to be suitable delivery vehicles for the stable introduction of genes of interest into the genome of a broad range of target cells. The ability of retroviral vectors to deliver unrearranged, single copy transgenes into cells makes retroviral vectors well suited for transferring genes into cells. Further, retroviruses enter host cells by the binding of retroviral envelope glycoproteins to specific cell surface receptors on the host cells. Consequently, pseudotyped retroviral vectors in which the encoded native envelope protein is replaced by a heterologous envelope protein that has a different cellular specificity than the native envelope protein (e.g., binds to a different cell-surface receptor as compared to the native envelope protein) may also find utility in practicing the present invention. The ability to direct the delivery of retroviral vectors encoding one or more target protein coding sequences to specific target cells is desirable in practice of the present invention.

The present invention provides retroviral vectors which include e.g., retroviral transfer vectors comprising one or more transgene sequences and retroviral packaging vectors comprising one or more packaging elements. In particular, the present invention provides pseudotyped retroviral vectors encoding a heterologous or functionally modified envelope protein for producing pseudotyped retrovirus.

The core sequence of the retroviral vectors of the present invention may be readily derived from a wide variety of retroviruses, including for example, B, C, and D type retroviruses as well as spumaviruses and lentiviruses (RNA Tumor Viruses, Second Edition, Cold Spring Harbor Laboratory, 1985). An example of a retrovirus suitable for use in the compositions and methods of the present invention includes, but is not limited to, a lentivirus. Other retroviruses suitable for use in the compositions and methods of the present invention include, but are not limited to, Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. Preferred Murine Leukemia Viruses include 4070A and 1504A (Hartley and Rowe, J. Virol. 19:19-25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Such retroviruses may be readily obtained from depositories or collections such as the American Type Culture Collection ("ATCC"; Rockville, Md.), or isolated from known sources using commonly available techniques.

Preferably, a retroviral vector sequence of the present invention is derived from a lentivirus. A preferred lentivirus is a human immunodeficiency virus, e.g., type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. Other lentiviruses include a sheep Visna/maedi virus, a feline immunodeficiency virus (FIV), a bovine lentivirus, simian immunodeficiency virus (SIV), an equine infectious anemia virus (EIAV), and a caprine arthritis-encephalitis virus (CAEV).

The various genera and strains of retroviruses suitable for use in the compositions and methods are well known in the art (see, e.g., Fields Virology, Third Edition, edited by B. N. Fields et al., Lippincott-Raven Publishers (1996), see e.g., Chapter 58, Retroviridae: The Viruses and Their Replication, Classification, pages 1768-1771, including Table 1.

The present invention provides retroviral packaging systems for generating producer cells and producer cell lines that produce retroviruses, and methods of making such packaging systems. Accordingly, the present invention also provides producer cells and cell lines generated by introducing a retroviral transfer vector into such packaging systems (e.g., by transfection or infection), and methods of making such packaging cells and cell lines.

The packaging systems of the present invention comprise at least two packaging vectors, a first packaging vector which comprises a first nucleotide sequence comprising a gag, a pol, or gag and pol genes and a second packaging vector which comprises a second nucleotide sequence comprising a heterologous or functionally modified envelope gene. In a preferred embodiment, the retroviral elements are derived from a lentivirus, such as HIV. Preferably, the vectors lack a functional tat gene and/or functional accessory genes (vif, vpr, vpu, vpx, nef). In a further preferred embodiment, the system further comprises a third packaging vector that comprises a nucleotide sequence comprising a rev gene. The packaging system can be provided in the form of a packaging cell that contains the first, second, and, optionally, third nucleotide sequences.

The invention is applicable to a variety of systems, and those skilled in the art will appreciate the common elements shared across differing groups of retroviruses. The description herein uses lentiviral systems as a representative example. However, all retroviruses share the features of enveloped virions with surface projections and containing one molecule of linear, positive-sense single stranded RNA, a genome consisting of a dimer, and the common proteins gag, pol and env.

Lentiviruses share several structural virion proteins in common, including the envelope glycoproteins SU (gp120) and TM (gp41), which are encoded by the env gene; CA (p24), MA (p17) and NC (p7-11), which are encoded by the gag gene; and RT, PR and IN encoded by the pol gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated, e.g., by mutation or deletion.

First generation lentiviral vector packaging systems provide separate packaging constructs for gag/pol and env, and typically employ a heterologous or functionally modified envelope protein for safety reasons. In second generation lentiviral vector systems, the accessory genes, vif, vpr, vpu and nef, are deleted or inactivated. Third generation lentiviral vector systems are preferred for use in practicing the present invention and include those from which the tat gene has been deleted or otherwise inactivated (e.g., via mutation).

Compensation for the regulation of transcription normally provided by tat can be provided by the use of a strong constitutive promoter, such as the human cytomegalovirus immediate early (HCMV-IE) enhancer/promoter. Other promoters/enhancers can be selected based on strength of constitutive promoter activity, specificity for target tissue (e.g., a liver-specific promoter), or other factors relating to desired control over expression, as is understood in the art. For example, in some embodiments, it is desirable to employ an inducible promoter such as tet to achieve controlled expression. The gene encoding rev is preferably provided on a separate expression construct, such that a typical third generation lentiviral vector system will involve four plasmids: one each for gagpol, rev, envelope and the transfer vector. Regardless of the generation of packaging system employed, gag and pol can be provided on a single construct or on separate constructs.

Typically, the packaging vectors are included in a packaging cell, and are introduced into the cell via transfection, transduction or infection. Methods for transfection, transduction or infection are well known by those of skill in the art. A retroviral/lentiviral transfer vector of the present invention can be introduced into a packaging cell line, via transfection, transduction or infection, to generate a producer cell or cell line. The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoding by the packaging vector.

Stable cell lines, wherein the packaging functions are configured to be expressed by a suitable packaging cell, are known. For example, see U.S. Pat. No. 5,686,279; and Ory et al., Proc. Natl. Acad. Sci. (1996) 93:11400-11406, which describe packaging cells. Further description of stable cell line production can be found in Dull et al., 1998, J. Virology 72(11):8463-8471; and in Zufferey et al., 1998, J. Virology 72(12):9873-9880.

Zufferey et al., 1997, Nature Biotechnology 15:871-875, teach a lentiviral packaging plasmid wherein sequences 3' of pol including the HIV-1 envelope gene are deleted. The construct contains tat and rev sequences and the 3' LTR is replaced with poly A sequences. The 5' LTR and psi sequences are replaced by another promoter, such as one which is inducible. For example, a CMV promoter or derivative thereof can be used.

Preferred packaging vectors may contain additional changes to the packaging functions to enhance lentiviral protein expression and to enhance safety. For example, all of the HIV sequences upstream of gag can be removed. Also, sequences downstream of the envelope can be removed. Moreover, steps can be taken to modify the vector to enhance the splicing and translation of the RNA.

Optionally, a conditional packaging system is used, such as that described by Dull et al., J. Virology 72(11):8463-8471, 1998. Also preferred is the use of a self-inactivating vector (SIN), which improves the biosafety of the vector by deletion of the HIV-1 long terminal repeat (LTR) as described, for example, by Zufferey et al., 1998, J. Virology 72(12):9873-9880. Inducible vectors can also be used, such as through a tet-inducible LTR.

Any vector for use in practicing the invention will include heterologous control sequences, such as a constitutive promoter, e.g., the cytomegalovirus (CMV) immediate early promoter, the RSV LTR, the MoMLV LTR, and the PGK promoter; tissue or cell type specific promoters including mTTR, TK, HBV, hAAT, regulatable or inducible promoters, enhancers, etc. Preferred promoters include the LSP promoter (Ill et al., Blood Coagul. Fibrinolysis 8S2:23-30, 1997), the EF1-alpha promoter (Kim et al., Gene 91(2):217-23, 1990) and Guo et al., Gene Ther. 3(9):802-10, 1996). Most preferred promoters include the elongation factor 1-alpha (EF1a) promoter, a phosphoglycerate kinase-1 (PGK) promoter, a cytomegalovirus immediate early gene (CMV) promoter, chimeric liver-specific promoters (LSPs), a cytomegalovirus enhancer/chicken beta-actin (CAG) promoter, a tetracycline responsive promoter (TRE), a transthyretin promoter (TTR), an simian virus 40 (SV40) promoter and a CK6 promoter. The sequences of these and numerous additional promoters are known in the art. The relevant sequences may be readily obtained from public databases and incorporated into vectors for use in practicing the present invention.

The present invention also contemplates the inclusion of a gene regulation system for the controlled expression of the coding sequence for two or more polypeptides or proteins of interest. Gene regulation systems are useful in the modulated expression of a particular gene or genes. In one exemplary approach, a gene regulation system or switch includes a chimeric transcription factor that has a ligand binding domain, a transcriptional activation domain and a DNA binding domain. The domains may be obtained from virtually any source and may be combined in any of a number of ways to obtain a novel protein. A regulatable gene system also includes a DNA response element which interacts with the chimeric transcription factor. This element is located adjacent to the gene to be regulated.

Exemplary gene regulation systems that may be employed in practicing the present invention include, the Drosophila ecdysone system (Yao et al., Proc. Nat. Acad. Sci., 93:3346 (1996)), the Bombyx ecdysone system (Suhr et al., Proc. Nat. Acad. Sci., 95:7999 (1998)), the Valentis GeneSwitch® synthetic progesterone receptor system which employs RU-486 as the inducer (Osterwalder et al., Proc Natl Acad Sci 98(22): 12596-601 (2001)); the Tet™ & RevTet™ Systems (BD Biosciences Clontech), which employs small molecules, such as tetracycline (Tc) or analogues, e.g. doxycycline, to regulate (turn on or off) transcription of the target (Knott et al., Biotechniques 32(4):796, 798, 800 (2002)); ARIAD Regulation Technology which is based on the use of a small molecule to bring together two intracellular molecules, each of which is linked to either a transcriptional activator or a DNA binding protein. When these components come together, transcription of the gene of interest is activated. Ariad has two major systems: a system based on homodimerization and a system based on heterodimerization (Rivera et al., Nature Med, 2(9): 1028-1032 (1996); Ye et al., Science 283: 88-91 (2000)), either of which may be incorporated into the vectors of the present invention.

Preferred gene regulation systems for use in practicing the present invention are the ARIAD Regulation Technology and the Tet™ & RevTet™ Systems.

Delivery of Nucleic Acid Constructs Including Protein or Polypeptide Coding Sequences to Cells The vector constructs of the invention comprising nucleic acid sequences encoding heterologous proteins or polypeptides, and a self-processing cleavage site alone or in combination with a sequence encoding an additional proteolytic cleavage site may be introduced into cells in vitro, ex vivo or in vivo for expression of heterologous coding sequences by cells, e.g., somatic cells in vivo, or for the production of recombinant polypeptides by vector-transduced cells, in vitro or in vivo.

The vector constructs of the invention may be introduced into cells in vitro or ex vivo using standard methodology known in the art. Such techniques include transfection using calcium phosphate, microinjection into cultured cells (Capecchi, Cell 22:479-488 (1980)), electroporation (Shigekawa et al., BioTechn., 6:742-751 (1988)), liposome-mediated gene transfer (Mannino et al., BioTechn., 6:682-690 (1988)), lipid-mediated transduction (Felgner et al., Proc. Natl. Acad. Sci. USA 84:7413-7417 (1987)), and nucleic acid delivery using high-velocity microprojectiles (Klein et al., Nature 327:70-73 (1987)).

For in vitro or ex vivo expression, any cell effective to express a functional protein may be employed. Numerous examples of cells and cell lines used for protein expression are known in the art. For example, prokaryotic cells and insect cells may be used for expression. In addition, eukaryotic microorganisms, such as yeast may be used. The expression of recombinant proteins in prokaryotic, insect and yeast systems are generally known in the art and may be adapted for protein or polypeptide expression using the compositions and methods of the present invention.

Exemplary host cells useful for expression further include mammalian cells, such as fibroblast cells, cells from non-human mammals such as ovine, porcine, murine and bovine cells, insect cells and the like. Specific examples of mammalian cells include COS cells, VERO cells, HeLa cells, Chinese hamster ovary (CHO) cells, 293 cell, NSO cells, 3T3 fibroblast cells, W138 cells, BHK cells, HEPG2 cells, DUX cells and MDCK cells.

Host cells are cultured in conventional nutrient media, modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium (MEM), Sigma), RPMI 1640 (Sigma), and Dulbecco's Modified Eagle's Medium (DMEM, Sigma) are typically suitable for culturing host cells. A given medium is generally supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The appropriate culture conditions for a particular cell line, such as temperature, pH and the like, are generally known in the art, with suggested culture conditions for culture of numerous cell lines for example in the ATCC Catalogue available on line at "http://www.atcc.org/SearchCatalogs/AllCollections.cfm"

The vectors of the invention may be administered in vivo via various routes (e.g., intradermally, intravenously, intratumorally, into the brain, intraportally, intraperitoneally, intramuscularly, into the bladder etc.), to deliver multiple genes connected via a self processing cleavage sequence to express two or more proteins or polypeptides in animal models or human subjects. Dependent upon the route of administration, the therapeutic proteins elicit their effect locally (e.g., in brain or bladder) or systemically (other routes of administration). The use of tissue specific promoters 5' to the open reading frame(s) for a protein or polypeptide in the vectors of the invention may be used to effect tissue specific expression of the two or more proteins or polypeptides encoded by the vector.

Various methods that introduce a recombinant vector carrying a transgene into target cells in vitro, ex vivo or in vivo have been previously described and are well known in the art. The present invention provides for therapeutic methods, vaccines, and cancer therapies by transducing target cells with recombinant vectors of the invention.

For example, in vivo delivery of the recombinant vectors of the invention may be targeted to a wide variety of organ types including, but not limited to brain, liver, blood vessels, muscle, heart, lung and skin.

In the case of ex vivo gene transfer, the target cells are removed from the host and genetically modified in the laboratory using recombinant vectors of the present invention and methods well known in the art.

The recombinant vectors of the invention can be administered using conventional modes of administration including but not limited to the modes described above. The recombinant vectors of the invention may be provided in any of a variety of formulations such as liquid solutions and suspensions, microvesicles, liposomes and injectable or infusible solutions. The preferred form depends upon the mode of administration and the therapeutic application. A from appropriate to the route of delivery may be readily determined using knowledge generally available to those of skill in the relevant art.

The many advantages to be realized in using the inventive recombinant vector constructs of the invention in recombinant protein and polypeptide production in vivo include administration of a single vector for long-term and sustained expression of two or more recombinant protein or polypeptide ORFs in patients; in vivo expression of two or more recombinant protein or polypeptide ORFs having biological activity; and the natural posttranslational modifications of the recombinant protein or polypeptide generated in human cells.

One preferred aspect is use of the recombinant vector constructs of the present invention for the in vitro production of recombinant proteins and polypeptides. Methods for recombinant protein production are well known in the art and self processing cleavage site-containing vector constructs of the present invention may be utilized for expression of recombinant proteins and polypeptides using such standard methodology.

In one exemplary aspect of the invention, vector introduction or administration to a cell (transfection) is followed by one or more of the following steps:

(1) culturing the transfected cell under conditions to selecting for a cell expressing the recombinant protein or polypeptide;

(2) evaluating expression of the recombinant protein or polypeptide; and (3) collecting the recombinant protein or polypeptide.

The objects of the invention have been achieved by a series of experiments, some of which are described by way of the following non-limiting examples.

EXAMPLES

Example 1

Expression of Two Secreted Proteins Using the FMDV 2A and IRES Sequences

In one exemplary application of the method described herein, the coding sequences for VEGF-TRAP and platelet factor 4 (PF4) were expressed from a single promoter using either a 2A sequence or an IRES. At present, the IRES represents the state of the art for expressing two proteins from a single promoter. The purpose of this experiment was to compare the protein expression from a vector containing a 2A or 2A-like sequence to that from a vector containing an IRES. A schematic depiction of the plasmids used in this experiment is provided in FIGS. 1A-D. Vector components include the following:

| | |
|---|---|
| CAG promoter | The cytomegalovirus enhancer/chicken beta-actin/Rabbit β-globin promoter (CAG promoter; Niwa H. et al. 1991. Gene 108(2): 193-9) |
| 2A | SEQ ID NO: 14 |
| Furin | SEQ ID NO: 15 |
| WPRE (Woodchuck Hepatitis Virus Post-Transcriptional Regulatory Element) | SEQ ID NO: 16 |
| bGHpolyA (Bovine Growth Hormone Polyadenylation Signal Sequence) | SEQ ID NO: 17 |
| EMCV IRES | A 492 base pair IRES obtainable from encephelomycarditis virus (EMCV) SEQ ID NO: 18 |
| sPF4 | pBLAST-hPF4 (Invivogen) and Tanaka, T. et al. Nat. Med. 3(4): 437-42, 1997. The hPF4 sequence was modified to contain a DLR mutation (Hagedorn et al. Cancer Res. 62: 6884-6890, 2002). The mutation was generated using a Quick-Change Site-Directed Mutagenesis Kit (Stratagene) and the following oligonucleotide primers:<br>sPF4(DLR) FOR: SEQ ID NO: 19<br>sPF4(DLR) REV: SEQ ID NO: 20 |
| VEGF-TRAP | R1 D2 FOR: SEQ ID NO: 21<br>R1 D2 REV: SEQ ID NO: 22<br>R2 D3 FOR: SEQ ID NO: 23<br>R2 D3 REV: SEQ ID NO: 24<br>FC FOR: SEQ ID NO: 25<br>FC REV: SEQ ID NO: 26<br>The signal sequence for VEGFR1 was generated using the oligonucleotides shown below and fused to the aforementioned chimeric fragment using standard molecular biology techniques.<br>R1 SS FOR: SEQ ID NO: 27<br>R1 SS REV: SEQ ID NO: 28 |

| | -continued |
|---|---|
| sPF4:F2A:<br>VEGF TRAP<br>and<br>VEGF TRAP: F2A:sPF4 | The sPF4 (DLR) and VEGF-TRAP coding sequences were initially cloned downstream of the CAG expression cassette as single proteins. These plasmids were used as the basis for connecting the two proteins using the F2A sequence, which was performed by PCR SOEing using the following oligonucleotide primers:<br>PF4-F2A FOR: SEQ ID NO: 29<br>PF4-F2A REV: SEQ ID NO: 30<br>F2A-VT FOR: SEQ ID NO: 31<br>F2A-VT REV: SEQ ID NO: 32<br>PF4 FOR: SEQ ID NO: 33<br>VT REV: SEQ ID NO: 34 |
| VEGF TRAP:EMCV IRES:sPF4<br>and<br>sPF4: EMCV IRES:VEGF TRAP | The ECMV IRES was PCR amplified with the primers listed below and cloned in between the sPF4 (DLR) and VEGF-TRAP nucleotide sequences using standard molecular biology procedures.<br>PF4-I-VT REV: SEQ ID NO: 35<br>VT-I-PF4 REV: SEQ ID NO: 36<br>IRES FOR: SEQ ID NO: 37 |

In these examples the 2A or IRES sequences were placed between the VEGF-TRAP and sPF4 coding sequence and the complete cassette was driven by the CAG promoter. Both orientations of the two genes relative to the F2A and IRES sequences were cloned and evaluated (FIGS. 1A-D). These plasmids were initially tested by transient transfection into 293T cells, which was performed in a 6-well dish using a FUGENE 6 kit (Roche). The transfections were done in triplicate using 2×10⁵ cells and 1□g of DNA per well, and 200 ng of a CAG-GFP expressing plasmid was added to each sample as a transfection control. Cell culture supernatants were harvested approximately 40 hours later and assayed for PF4 expression using an Asserachrom PF4 ELISA assay (Diagnostica Stago). The VEGF-TRAP protein contains domain 2 of VEGFR1 and domain 3 of VEGFR2 connected to the human IgG Fc domain, and is detected with a human IgG ELISA kit (Bethyl Laboratories) using recombinant VEGFR1-Fc (R & D Systems) to generate a standard curve. The cells were harvested and subjected to FACs analysis for GFP expression. The results of these assays are shown in FIGS. 2A-C. In the IRES containing vectors, the gene upstream of the IRES is expressed at high levels whereas the gene downstream of the IRES is very poorly expressed. This is in striking contrast to the F2A containing vectors, which expressed both proteins at equal levels. Expression levels of the two proteins are almost identical when placed either upstream or downstream F2A site, indicating that the F2A sequence appears to function independent of orientation/position. These data show that the F2A provides a significant improvement over the state of the art in expressing two genes from a single promoter.

Example 2

Expression of Human Factor VIII from a 2A Construct

We previously demonstrated that the 2A sequence can be used to efficiently express the heavy and light chains of human and rat monoclonal antibodies. (See, e.g., U.S. Ser. No. 60/540,554.) In this example a 2A sequence was evaluated as for its ability to express the heavy and light chains human of Factor VIII using a single promoter. A typical Factor VIII expression construct includes a promoter, a Factor VIII heavy chain coding sequence, a furin cleavage site (RAKR (SEQ ID NO: 38)), a 2A sequence, a Factor VIII light chain coding sequence, and a polyA sequence (FIG. 3). FIG. 4 shows four exemplary methods of linking the heavy and light chains of human Factor VIII to a self-processing cleavage site (e.g., 2A) with and without an additional proteolytic cleavage site (e.g., RAKR (SEQ ID NO: 38)) are under evaluation. These constructs were designed to express a B domain deleted form of Factor VIII based on the 'SQ' B-domain deletion (Lind et al., Eur. J. Biochem. 232:19-27, 1995), which fuses Ser 743 to Glu 1638, and is identical to the B-domain deletion in Refacto, a licensed recombinant Factor VIII product (Eriksson et al., Semin. Hematol. 38:24-31, 2001). In the native Factor VIII protein, QN is repeated at amino acids 744 and 1638. For these studies, QN was left at the 5' end of the B-domain deletion. Previous data where Factor VIII heavy and light chains were separately expressed indicated that the heavy chain was more stable with the addition of these extra two amino acids (Yonemura et al., Protein Eng. 6: 669-674 (1993)). In each of the exemplary constructs shown in FIG. 4, a human IgG signal peptide (SS) is cloned upstream of the light chain. It has previously been shown that when joining two proteins with a self processing sequence such as 2A, the C-terminal protein requires a signal sequence for efficient secretion (de Felipe et al., J. Biol. Chem. 278: 11441-11448, 2003). In construct D1, both the endogenous Factor VIII cleavage sites, as well as an additional furin (RAKR (SEQ ID NO: 38)) and 2A cleavage site are present. The D2 and E1 constructs have the endogenous furin and thrombin cleavage sites removed, respectively. The E2 construct contains both endogenous cleavage sites and a 2A sequence, but is missing the additional furin site.

Figure 5:
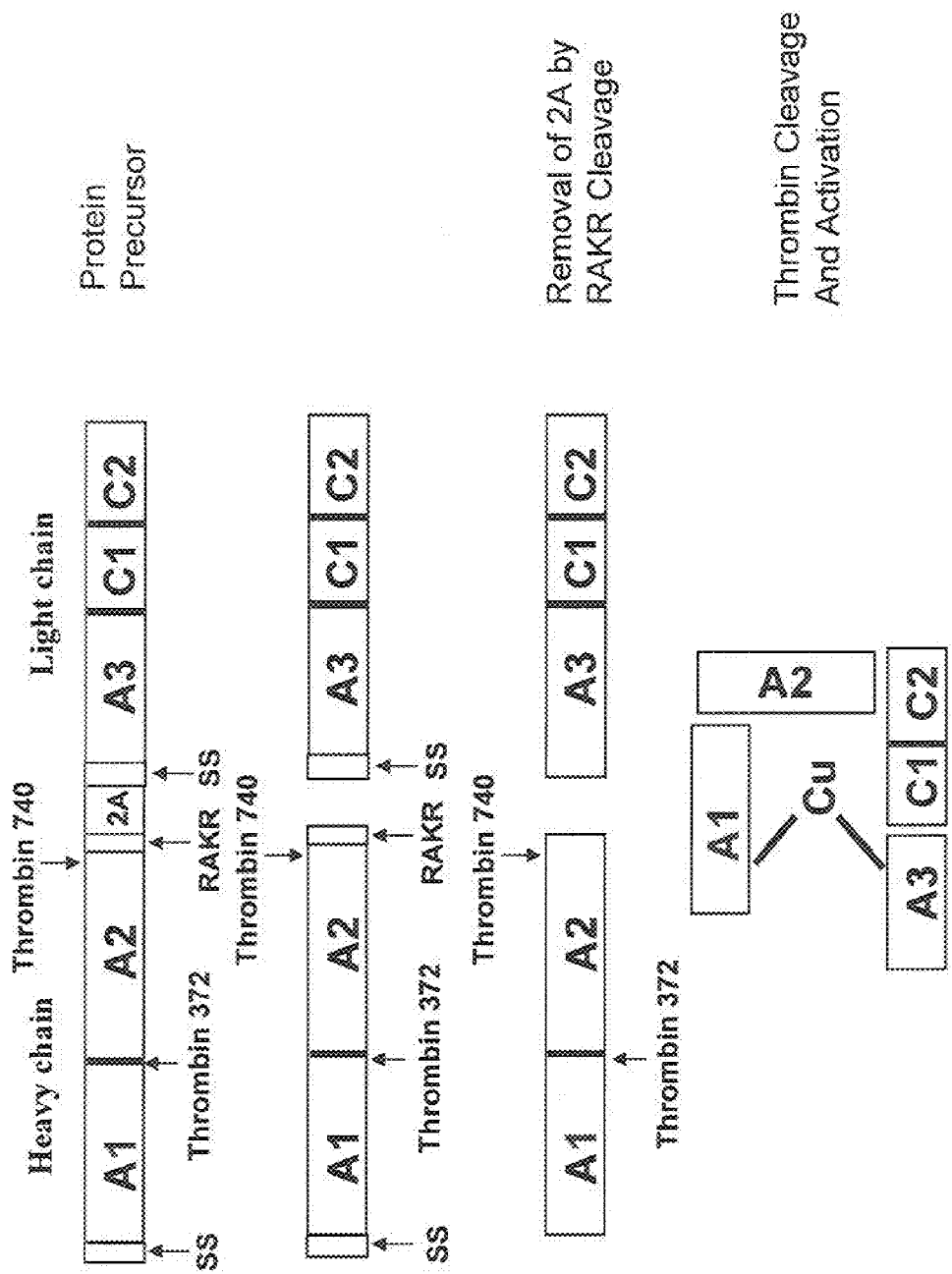
FIG. 5 is a schematic illustration of the bioprocessing of Factor VIII heavy and light chains when they are expressed using a FVIII H2AL (heavy chain-2A sequence-light chain) expression cassette comprising a 2A self-processing cleavage site and an additional proteolytic cleavage site (Furin). 'RAKR' is disclosed as SEQ ID NO: 38.

The processing of the D1 construct is diagrammed in FIG. 5. The 2A site is initially cleaved during protein translation. The signal sequence is subsequently cleaved and the furin cleavage and removal of the 2A sequence can then takes place due to the presence of the RAKR (SEQ ID NO: 38) sequence. The final thrombin cleavage and Factor VIII activation typically occur in the plasma. A cell line expressing this construct will produce Factor VIII recombinant protein that does not contain any additional amino acids.

When these constructs are transiently transfected into cell lines, e.g., CHO, BHK, and 293, cell culture supernatants and lysates are examined for Factor VIII activity using the Coamatic assay, Factor VIII protein expression by ELISA, and Factor VIII cleavage and secretion by Western blot analysis. These analyses are generally typically used by those of skill in the art to evaluate the relative efficiency of expression, cleavage, and secretion of Factor VIII protein.

Example 3

Expression of a Rat IgG from an AAV H2AL Plasmid Transfected into 293 T Cells

Figure 6:
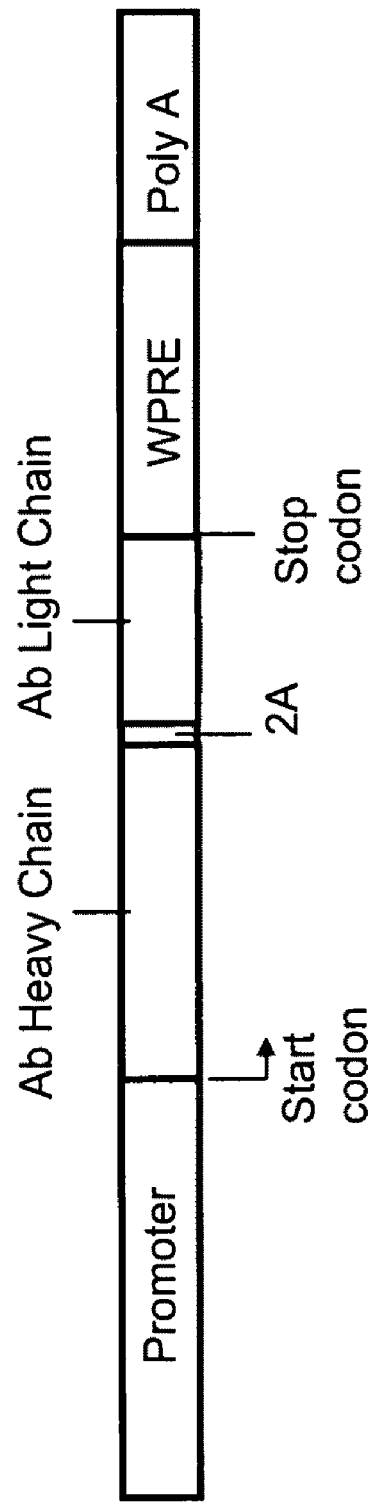
FIG. 6 is a schematic illustration of an exemplary expression cassette for expression of monoclonal antibody heavy and light chains where the cassette comprises a 2A self-processing cleavage site, as described in Example 3.
Figure 7:
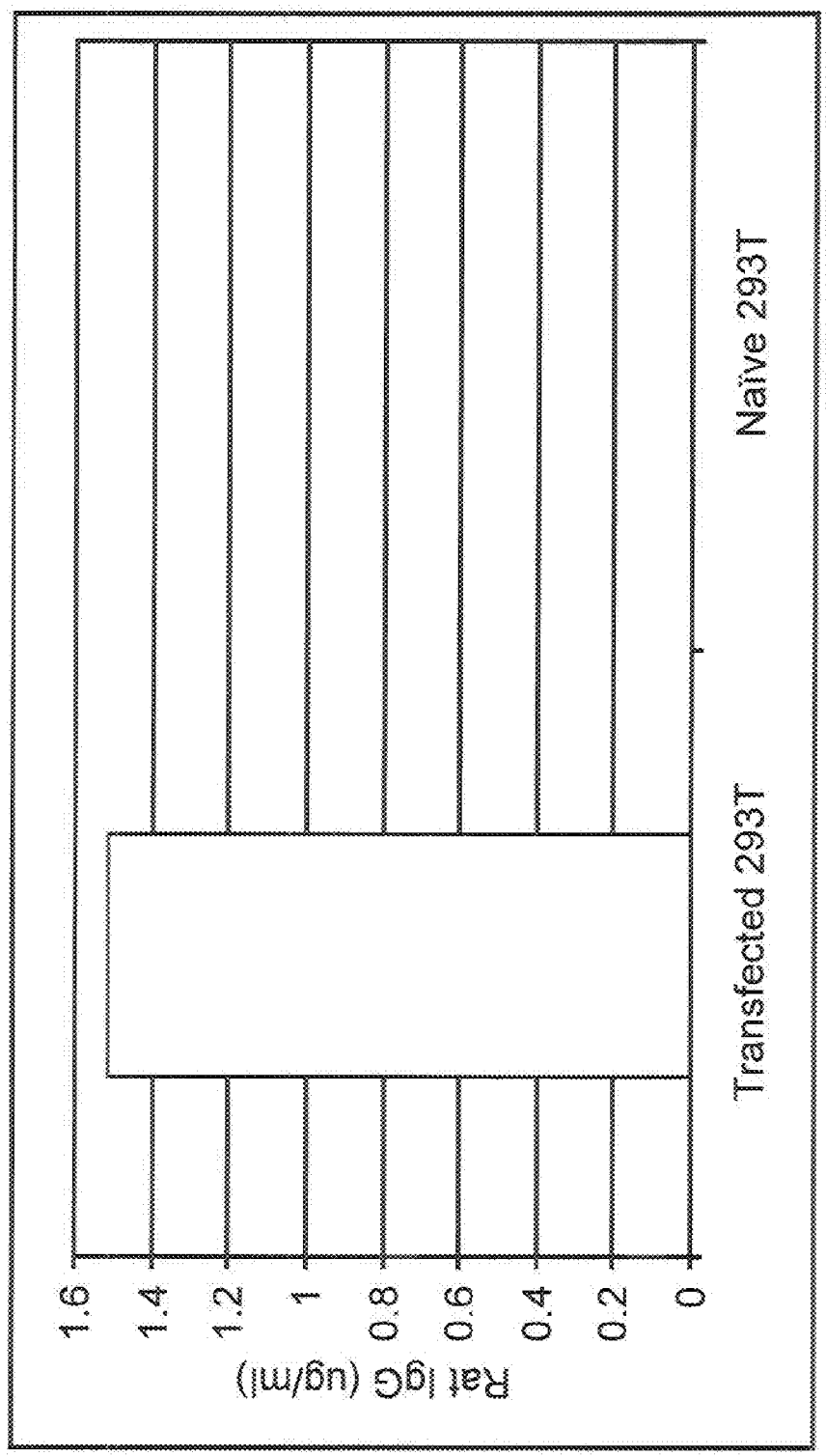
FIG. 7 demonstrates the expression of a full length rat anti-FLK-1 monoclonal antibody (IgG) in the supernatant of 293T cells transfected with an anti-FLK-1/AAV H2AL (heavy chain-2A sequence-light chain) plasmid.

An AAV plasmid (pAAV H2AL) encoding the heavy and light chain of a monoclonal IgG antibody against murine FLK-1 and linked by insertion of the FMDV 2A sequence (FIG. 6), was transiently transfected into 293T cells. Cells were grown in Iscove's Modified Dulbecco's Medium (IMDM) supplemented with 10% fetal bovine serum, 1% L-glutamine, and 1% penicillin-streptomycin solution (Invitrogen). Transfection was carried out using a FuGENE 6 transfection kit (Roche). pAAV H2AL plasmid DNA was mixed with the transfection reagent according to the manufacturer's instruction and the DNA-lipid mixture was added to the cell culture medium. The transfected cells were incubated for 48 or 72 hours and the supernatants analyzed for antibody expression. The mAb concentration was determined using a rat IgG ELISA assay (Bethyl Laboratories), in which mAb IgG protein was captured by an immobilized anti-rat IgG antibody on ELISA plates and detected by an anti-rat IgG Fc antibody conjugated with HRP. The ELISA plates were developed and mAb concentrations were calculated based on OD reading of the samples as compared to a standard curve with known rat IgG concentrations. ELISA assay results revealed that the recombinant rat IgG antibody was expressed at high levels in the supernatant of 293T cells transfected with the AAV plasmid containing a 2A sequence (FIG. 7).

The biological activity of the antibody was evaluated for neutralizing activity in a VEGF-FLK-1 binding assay. In this assay, recombinant VEGF (vascular endothelial cell growth factor, from R & D Systems) was coated on ELISA plates (Nunc), then blocked with 5% milk. The rat anti-FLK-1 antibody was pre-incubated at various concentrations with recombinant FLK-1-Fc (R & D Systems). The antibody/FLK-1 mixture was transferred to ELISA wells and the plates were incubated to allow VEGF-FLK-1 binding. After rinsing with balance solution, a goat anti-FLK-1 antibody conjugated with biotin was used to detect bound FLK-1, which was visualized by streptavidin-HRP (PharMingen) after color development with the HRP substrate.

Figure 8:
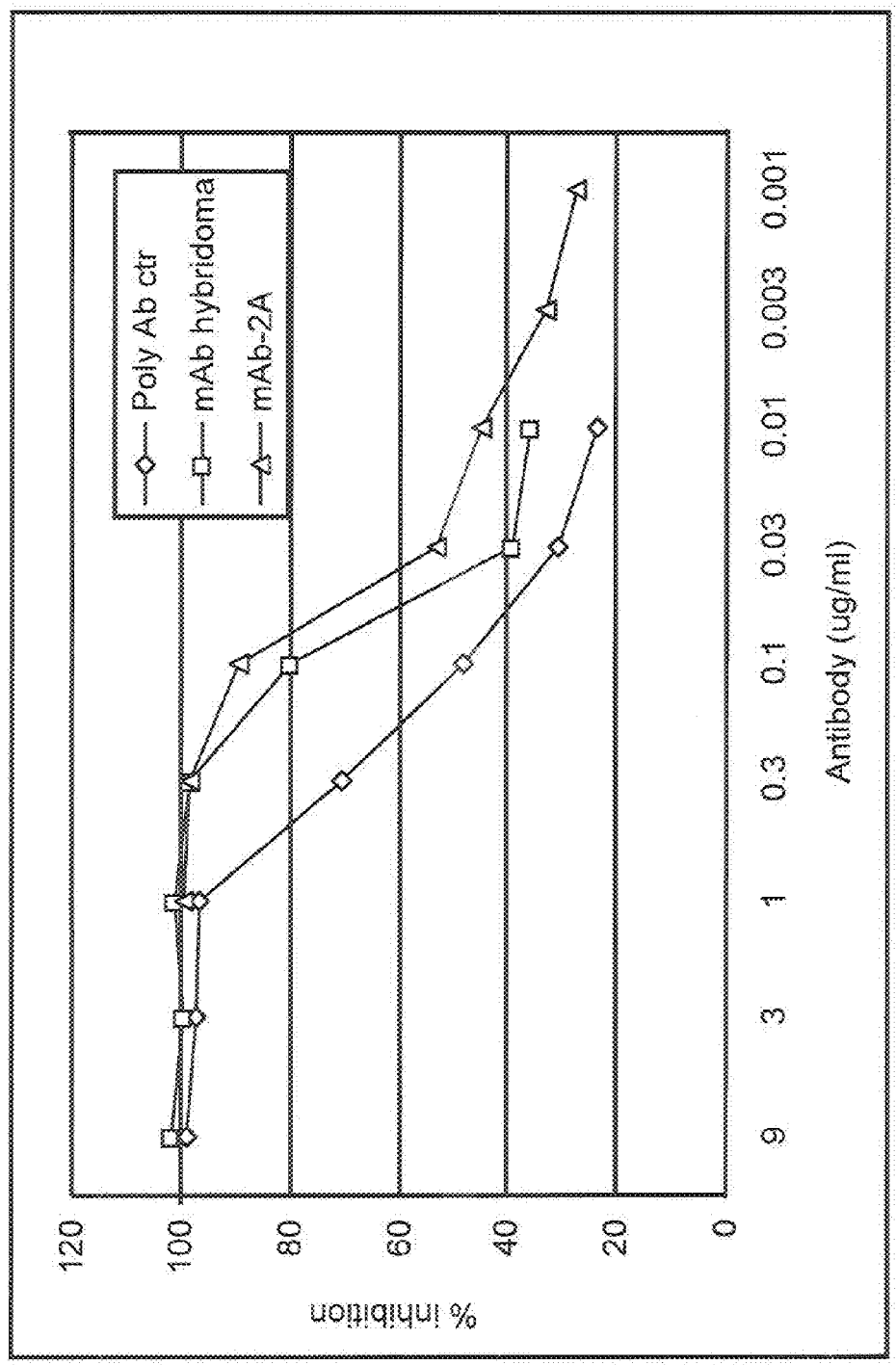
FIG. 8 demonstrates the biological activity of rat anti-FLK-1 antibody (IgG) expressed in 293T cell supernatants transfected with an anti-FLK-1 Ig/AAV H2AL plasmid.

By using the VEGF/FLK-1 (ligand-receptor) binding assay, it was demonstrated that the antibody expressed from 293T cells following transient transfection exhibits full biological activity, similar to that of the native antibody expressed by parent hybridoma cells (FIG. 8).

The antibody expressed from the plasmid utilizing the self processing 2A sequence was further characterized using Western blot analysis. Protein in the supernatant of transiently transfected 293T cells (transfected with AAV H2AL plasmid) or from that of hybridoma cells was separated by polyacrylamide gel electrophoresis under reducing or non-reducing conditions. For the reducing gel, protein samples were mixed with 2×LDS sample buffer (Invitrogen), boiled, loaded on pre-cast 12% Tris-Glycine gel (Invitrogen), and run with Tris-Glycine SDS running buffer. For the non-reducing gel, protein samples were mixed with 2× native TrisGly sample buffer (Invitrogen), loaded on pre-cast 12% Tris-Glycine gel (Invitrogen), and run with Tris-Glycine native running buffer (Invitrogen). After electrophoresis, the proteins were transferred to nitrocellulose membranes in Tris-Glycine transfer buffer with 20% methanol. The membranes were blocked with blocking solution and stained with HRP-conjugated anti-rat IgG. The membrane blots were treated using reagents provided in a SuperSignal West Chemiluminescent substrate kit (Pierce) and protein bands were visualized in Biome film (Kodak).

Figure 9B:
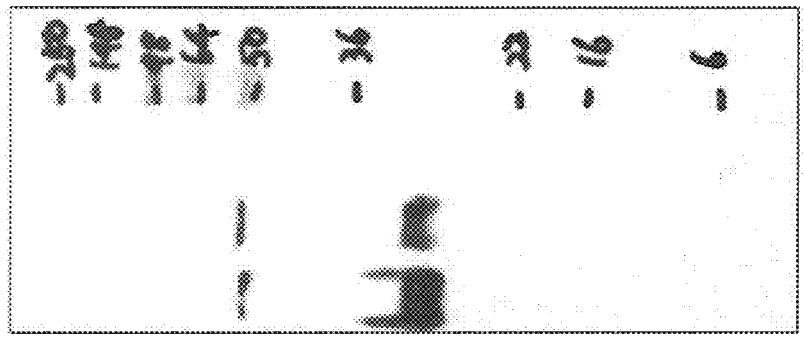
Figure 9A:
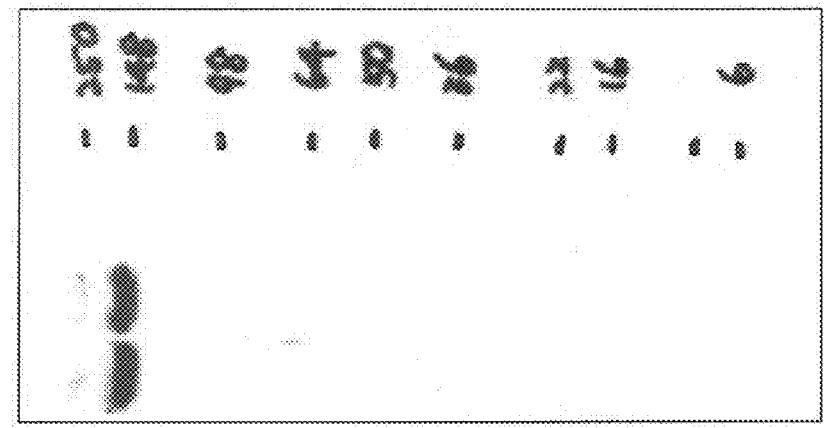
FIGS. 9A and B show the results of Western blot analysis of rat anti-FLK-1 antibody (IgG) in 293T cell supernatants following transfection of an anti-FLK-1 Ig/AAV H2AL plasmid.

Western blot analysis revealed that the antibodies from both the parental hybridoma cell line and the transfected 293T cells appear as an approximately 160 kD band on a non-reducing gel (FIG. 9A). This indicates that the heavy and light chains generated via the 2A cleavage site dimerize properly with a heavy and light chain ratio of 1:1, given that no additional bands, such as an approximately 133 kD band which would indicate a heavy to light chain ratio of 2:1, were detected. On a reducing gel, the antibodies from both hybridoma and transfected 293T cells appeared as an approximately 55 kD band (heavy chain) and a 23 kD band (light chain). No uncleaved 78 kD precursor polyprotein was detected, indicating efficient cleavage by the 2A peptide (FIG. 9B). Antibody expressed from the H2AL construct appeared to have a slightly larger molecular weight, which may be due to the additional amino acid residues contributed by the 2A sequence.

These results demonstrate that the 2A sequence provided a "cleavage" site facilitating the generation of both chains of the IgG molecule during the translation process in 293T cells. In other words, the chimeric H2AL polyprotein underwent autolytic cleavage to yield a full length, intact Ig molecule containing two heavy chains and two light chains following dimerization.

Example 4

Expression of a Human Immunoglobulin from an AAV H2AL Construct

In another example used to illustrate the invention, an AAV construct comprising a self processing cleavage site was used to express the heavy and light chain of a human monoclonal antibody directed to KDR. An AAV vector comprising a sequence encoding a novel human anti-VEGFR2 (KDR) mAb heavy chain, a sequence encoding a self-processing 2A cleavage site, and a sequence encoding a human anti-VEGFR2 (KDR) mAb light chain was constructed using the same strategy described in Example 3. The AAV vector also contains an EF1-alpha or CAG promoter, a WPRE, and poly A sequence. 293T cells were transfected with the AAV plasmid using a FuGENE 6 kit based on the manufacture's instructions and cell supernatants were harvested 48 or 72 hours post-transfection. The concentration of the mAb in 293T cell supernatants was determined using a sandwich ELISA assay for human IgG (Bethyl Laboratories). In this assay, human IgG was captured by an immobilized anti-human IgG antibody on ELISA plates and detected by an anti-human IgG Fc antibody conjugated with HRP. Color was developed after adding substrate solution to the wells and mAb concentrations were calculated based on OD reading of the samples with the human IgG of known concentrations as a standard curve.

Figure 10:
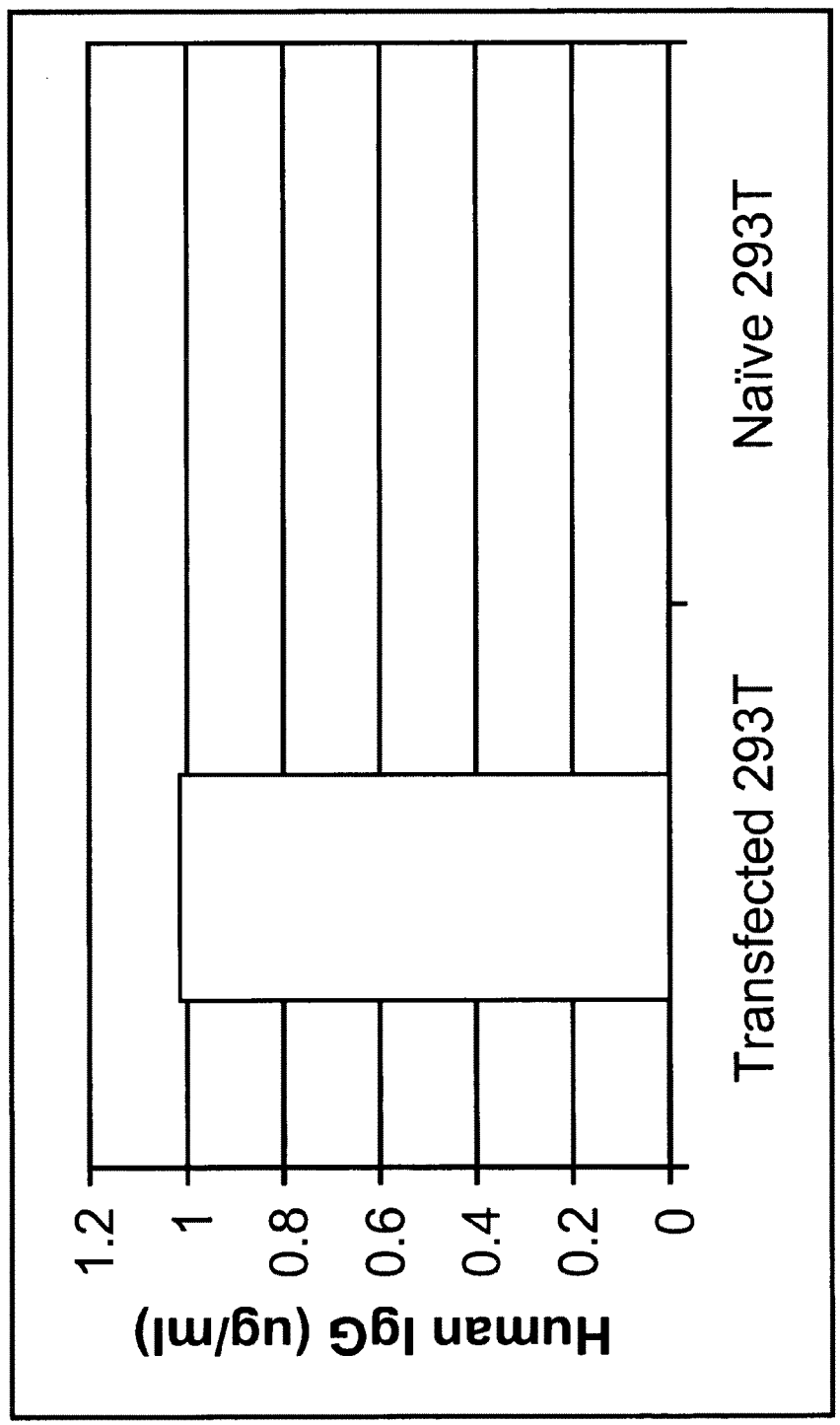
FIG. 10 demonstrates the expression of a full length human anti-KDR monoclonal antibody (IgG) in the supernatant of 293T cells transfected with anti-KDR/AAV H2AL plasmid.

The results demonstrate that transfection of an AAV plasmid encoding the heavy and light chains of a human antibody linked by a sequence encoding a self-processing 2A cleavage site into 293T cells resulted in high level expression of a full length antibody in cell culture supernatants (FIG. 10). These results show that heavy and light chains of a human antibody can be generated from a single open reading frame using a vector comprising a sequence encoding a self-processing 2A cleavage site which results in autocleavage. Furthermore, the heavy and light chains are folded and secreted properly.

Example 5

In Vivo Expression of a Full-Length Rat Anti-Flk-1 Monoclonal Antibody by a 2A Self-Processing Sequence Containing AAV Vector In another example of the invention, two polypeptides, specifically IgG heavy and light chains of a rat anti-FLK-1 monoclonal antibody, were expressed in vivo from a single promoter using a rAAV vector. Delivery of monoclonal antibodies by gene therapy has a number of advantages relative to conventional methods currently used in the clinic. rAAV is a preferred gene therapy viral system due to its safety profile and sustained gene expression. In this invention, a rAAV-6 vector was constructed to contain an AAV ITR, a CAG promoter, and polyA sequences. The vector includes a single open reading frame comprising in the 5' to 3' direction, the coding sequence for a rat IgG heavy chain, the coding sequence for a self processing 2A sequence, and the coding sequence for an antibody light chain, engineered and cloned into the vector operatively linked to the CAG promoter. The total size of the rAAV construct is within the size limit of rAAV and viral particles are effectively packaged as demonstrated by viral production in 293 cells.

Replication-deficient rAAV virus was generated in 293 cells using AAV plasmid transfection in the presence of adenovirus. rAAV viruses were purified by CsCl2 gradient centrifugation and the physical titers determined by dot blot. Purified rAAV was used to infect 293 cells or U87 glioma cells and monoclonal antibody concentrations in supernatants were measured by a rat IgG ELISA as described in Example 3.

Figure 11:
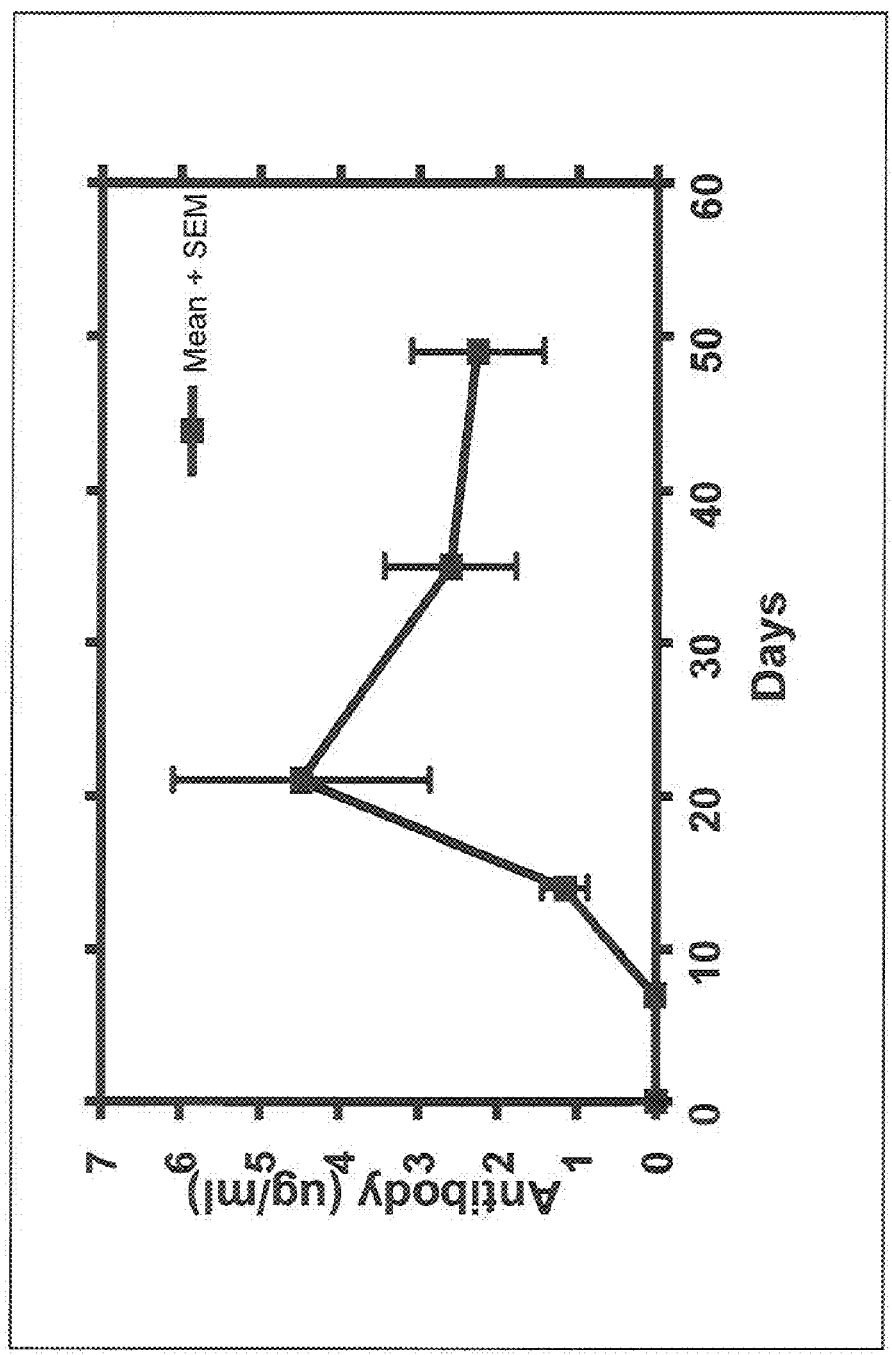
FIG. 11 shows the serum levels of a rat anti-FLK-1 monoclonal antibody (IgG) in mice injected with AAV6H2AL virus.

For antibody expression in vivo, $2 \times 10^{11}$ viral particles were administered by intramuscular (IM) injection into mice. Mice were bled at various time points. The monoclonal antibody level in serum was quantified using the rat IgG ELISA assay described in Example 3. The results showed that high levels of monoclonal antibodies were detected following IM injection of rAAV-6 that encodes full length rat anti-FLK-1 antibody (FIG. 11). Expression reached a maximum level of 4.5 ug/ml and a stable expression level of about 2.5 □g/ml was detected. The highest serum antibody level detected in any individual mouse was above 9 ug/ml (day 21).

These results demonstrate that full length mAb heavy and light chain proteins were successfully expressed at high levels in mice by use of vectors comprising a 2A self-processing sequence, demonstrating that 2A self-processing sequence mediated separation of antibody heavy and light chains takes place in vivo consistent with in vitro expression. Accordingly, the present invention provides a means to deliver therapeutic antibodies to patients in vivo in order to achieve a long term therapeutic effect. The expression cassette used in this study can easily be adapted to other vector systems, such as lentivirus, adenovirus, etc, using routine technology routinely employed by those of skill in the art.

Example 6

Figure 12:
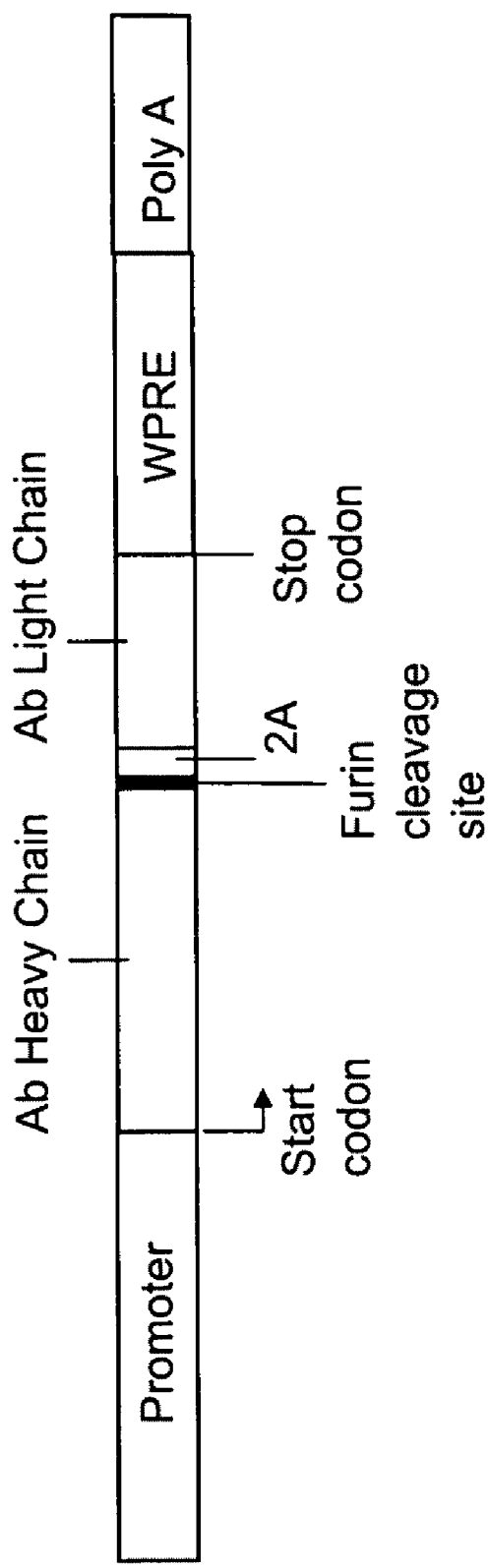
FIG. 12 depicts an expression cassette encoding an antibody heavy chain, an additional proteolytic cleavage site (Furin), a self-processing 2A cleavage site, and an antibody light chain (HF2AL) for a rat anti-FLK-1 antibody as described in Example 6.

Removal of 2A Cleavage Site Residues from Antibodies Expressed via an AAV HF2AL Vector Antibody heavy chains expressed using the H2AL constructs described above carry amino acid residues derived from the self processing cleavage sequence such as a 2A or 2A-like sequence at their C-terminus, which remain following self cleavage. To further optimize the expression system of the invention, a vector/plasmid was constructed which includes a protease cleavage site between the first polypeptide, i.e. the antibody heavy chain in this particular construct, and the self processing 2A sequence. The cleavage site used in the construct was RAKR (SEQ ID NO: 38), which belongs to the category of furin cleavage consensus sequences RXK(R)R (SEQ ID NO:10). Expected cleavage occurs between A and K in this cleavage site by furin or other proteases. The construct consists The construct comprises in the 5' to 3' direction: a CAG promoter, an antibody heavy chain coding sequence, a furin cleavage site coding sequence, a 2A cleavage site coding sequence, an antibody light chain coding sequence, and a polyA sequence (CAG HF2AL) (FIG. 12).

Figure 13:
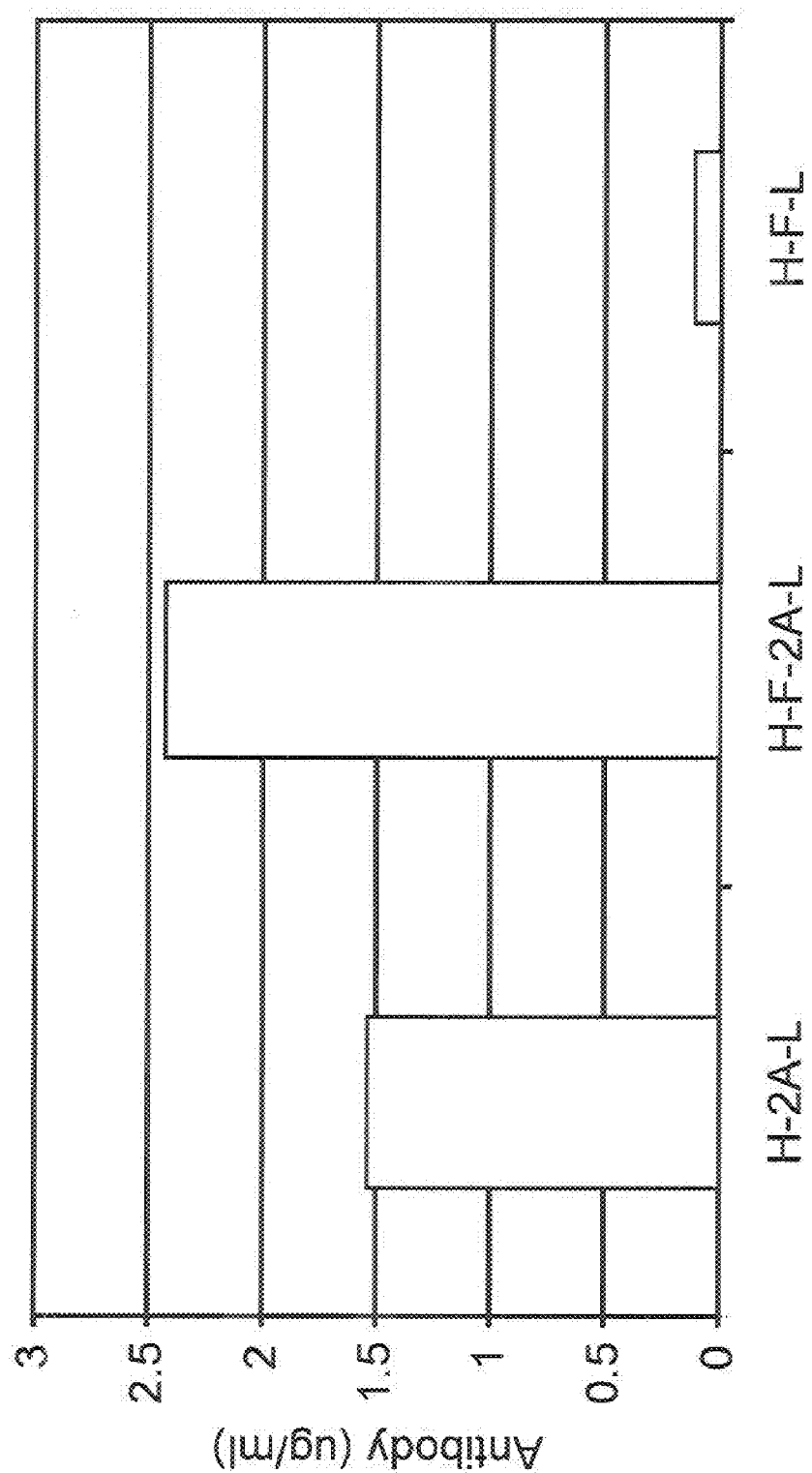
FIG. 13 shows expression of a rat anti-FLK-1 antibody in 293T cell supernatants transfected with a plasmid comprising a sequence encoding an antibody heavy chain and an antibody light chain together with a self-processing 2A cleavage site with and without a furin cleavage site, as described in Example 6.

To express the antibody from the CAG HF2AL construct, plasmid DNA was purified using a Qiagen plasmid DNA purification kit and used to transfect 293T cells in 6 well tissue culture plates using the FuGENE 6 kit (Roeche). The next day, cells were fed with serum-free medium and the conditioned media were harvested after 48 hours. In one control experiment, 293T cells were transfected with H2AL plasmid, which contains the same antibody and 2A sequence but lacks the furin cleavage site between the heavy chain and the 2A sequence. In the second control experiment, 293T cells were transfected with HFL plasmid, which contains the antibody heavy chain, the furin cleavage site, and the antibody light chain, but lacks the 2A sequence. Antibody concentrations in conditioned media were determined by ELISA. As shown in FIG. 13, the HF2AL construct gave higher antibody expression levels in supernatants from transfected cells than the H2AL construct. On the other hand, only very limited amount of antibody was detected in 293T cell supernatant transfected with the HFL (heavy chain-furin-light chain) construct.

The efficiency of removal of the additional 2A amino acid residues from the heavy chain of the antibody using a furin cleavage site was evaluated by separating antibodies in supernatants of HF2AL and H2AL transfected cells on a 12% Tris-Glycine SDS-PAGE gel under reducing conditions. The separated proteins were transferred onto a nitrocellulose membrane and the protein band for the antibody heavy chain was detected by a rabbit anti-rat antibody. This Western blot analysis showed that the antibody heavy chains expressed from the HF2AL plasmid in 293T cells migrated as a single band at a molecular weight that was smaller than the heavy chains expressed from the H2AL construct but similar to the antibody heavy chains expressed by parental hybridoma cells. This result suggests that the furin cleavage site within the HF2AL construct provides an efficient means to remove residual 2A derived amino acids.

Example 7

Expression of Antibodies in Furin −/− Cells Following Transfection with AAV Plasmids Containing a 2A Site and Furin Cleavage Site Furin is a ubiquitous subtilisin-related serine protease that is expressed in almost all cell types. Two cell lines, LoVo and CHO mutant RPE.40, have been found to have no functional furin due to mutations. Given that the furin cleavage site RAKR (SEQ ID NO: 38) used in the CAG HF2AL construct (Example 6) can be cleaved by furin as well as many other members of proteases in the same family, an experiment was conducted to identify the actual enzyme responsible for the cleavage of RAKR (SEQ ID NO: 38) in the antibody expressed from the CAG HF2AL construct. Plasmids with or without a furin cleavage site (HF2AL or H2AL) were used to transfect LoVo cells. LoVo is a human colon carcinoma cell line with no functional furin due to one nucleotide deletion in the region covering the homo B domain essential for the endoproteolytic activity to RXK(R)R (SEQ ID NO: 10) (Takahashi et al., Biochem Biophys Res Commun. 195: 1019-26. (1993)).

Figure 14:
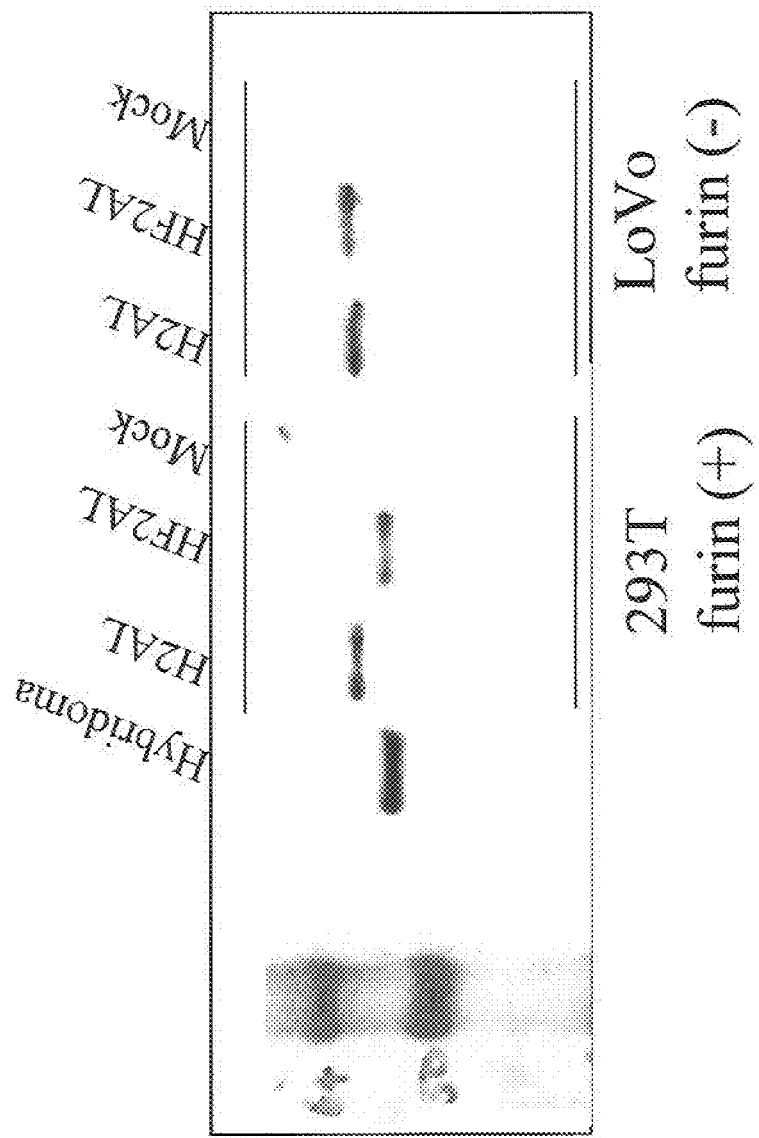
FIG. 14 shows Western blot characterization of an antibody heavy chain expressed from 293T (furin +) and LoVo (furin −) cells transfected with H2AL and HF2AL constructs as described in Example 6 and 7.

Following HF2AL and H2AL plasmid transfection into LoVo cells using the FuGENE 6 kit, cell culture supernatants were harvested from tissue culture dishes. Proteins were separated in a 12% Tris-Glycine SDS-PAGE gel under reducing conditions and analyzed in Western blot analysis, as described in Example 3. Results showed that the antibody heavy chains expressed from the HF2AL plasmid migrated at a molecular weight similar to the heavy chains expressed from the H2AL construct but higher than the antibody heavy chain expressed by parental hybridoma cells (FIG. 14). These results demonstrate that in LoVo cells which lack furin activity, additional amino acids derived from the 2A cleavage site remain at the C-terminus of the antibody heavy chain, confirming that the protease furin is the actual enzyme responsible for removal of 2A residues from the antibody when expressed in furin containing cells, such as 293T cells.

To further confirm the removal of residual amino acids from the 2A peptide sequence at the C terminus of the heavy chain expressed from the HF2A vector, the C-terminal fragment of the antibody heavy chain was analyzed by mass spectrum analysis. An expression vector was constructed that contains the rat antibody heavy chain, a furin cleavage site adjacent to the 2A cleavage site (RAKR (SEQ ID NO: 38)), the antibody light chain, and 6 his amino acids (HF2AL 6H), called "His-Tag". The plasmid was injected into mice via hydrodynamic gene transfer. The his-tagged monoclonal antibody was purified from mouse serum under native conditions using a Nickel column (Qiagen). The antibody heavy and light chains were separated on a 10% SDS-PAGE gel stained with Coomassie blue. The antibody heavy chain band was isolated from the SDS-PAGE gel and subjected to mass spectrum analysis after trypsin digestion. Mass spectrum data confirmed the removal of all but two amino acids derived from the 2A/furin sequences at the C terminus of the antibody heavy chain. Furthermore, by using combination of mass spectrum and PSD (MS/MS) sequencing analyses, it could be shown that the antibody heavy chain expressed from the HF2AL construct has the C-terminal sequence "SLSH-SPGKRA" (SEQ ID NO: 42), which includes native rat IgG heavy chain C-terminal amino acids plus two additional amino acids (RA) derived from the furin cleavage site.

In summary, the results provided herein demonstrate that residual amino acids derived from a self processing cleavage sequence, such as a 2A or 2A-like sequence can be efficiently removed during protein expression and secretion by introducing an additional proteolytic cleavage site (i.e., a furin cleavage site) adjacent to the 2A cleavage site. Removal of 2A sequence derived amino acids results in generation of a product lacking foreign amino acid residues which could otherwise elicit immune responses when administered in vivo. Furthermore, these data suggest that the addition of a furin cleavage site in 2A containing constructs results in an overall increase in antibody expression level.

What is claimed is:

1. An oligonucleotide construct for expression of a recombinant antibody or a recombinant antibody fragment having antigen-binding activity, wherein the antibody fragment is selected from the group consisting of Fab, F(ab')$_2$, Fv(scFv) and Fv antibody fragments, the oligonucleotide construct comprising, in the 5' to 3' direction, a promoter operably linked to all of (1) a coding sequence for a heavy chain of the antibody or a fragment of the heavy chain, (2) a coding sequence for a furin cleavage site, (3) a coding sequence for a 2A self-processing cleavage site and (4) a coding sequence for a light chain of the antibody or a fragment of the light chain.

2. The oligonucleotide construct of claim 1 wherein the 2A self-processing cleavage site is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8 and SEQ ID NO:9.

3. The oligonucleotide construct of claim 1 wherein the coding sequence for the 2A self processing cleavage site is SEQ ID NO:14.

4. The oligonucleotide construct of claim 1 wherein the 2A self processing cleavage site is SEQ ID NO:6.

5. The oligonucleotide construct of claim 1 wherein for the furin cleavage site has the consensus sequence SEQ ID NO:10.

6. The oligonucleotide construct of any one of claims 1-5 wherein the promoter is selected from the group consisting of an elongation factor 1-alpha promoter (EF1α) promoter, a phosphoglycerate kinase-1 promoter (PGK) promoter, a cytomegalovirus immediate early gene promoter (CMV), a chimeric liver-specific promoter (LSP), a cytomegalovirus enhancer/chicken beta-actin promoter (CAG), a tetracycline responsive promoter (TRE), a transthyretin promoter (TTR), a simian virus 40 promoter (SV40) and a CK6 promoter.

* * * * *